US011734901B2

(12) United States Patent
Jones et al.

(10) Patent No.: US 11,734,901 B2
(45) Date of Patent: *Aug. 22, 2023

(54) SURGEON HEAD-MOUNTED DISPLAY APPARATUSES

(71) Applicant: GLOBUS MEDICAL, INC., Audubon, PA (US)

(72) Inventors: Kenneth Milton Jones, Wellesley Hills, MA (US); John Popoolapade, Arlington, VA (US); Thomas Calloway, Pelham, NH (US); Thierry Lemoine, St. Germain du Corbeis (FR); Christian Jutteau, Orgeval (FR); Christophe Bruzy, Cergy (FR); Yannick James, Cergy (FR); Joachim Laguarda, Cergy (FR); Dong-Mei Pei Xing, Cergy (FR); Sebastien Gorges, St. Jean de Moirans (FR); Paul Michael Yarin, Cambridge, MA (US)

(73) Assignee: Globus Medical, Inc., Audubon, PA (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/533,169

(22) Filed: Nov. 23, 2021

(65) Prior Publication Data

US 2022/0084298 A1    Mar. 17, 2022

Related U.S. Application Data

(63) Continuation of application No. 16/842,839, filed on Apr. 8, 2020, now Pat. No. 11,217,028, which is a
(Continued)

(51) Int. Cl.
*G06T 19/00* (2011.01)
*G06F 3/01* (2006.01)
(Continued)

(52) U.S. Cl.
CPC ............ *G06T 19/006* (2013.01); *A61B 34/10* (2016.02); *A61B 90/37* (2016.02); *G06F 3/011* (2013.01);
(Continued)

(58) Field of Classification Search
CPC ....... G06T 19/006; G06T 19/20; A61B 34/10; A61B 90/37; G06F 3/011; G06F 3/012
(Continued)

(56) References Cited

U.S. PATENT DOCUMENTS 4,150,293 A    4/1979    Franke
4,722,056 A    1/1988    Roberts et al.
(Continued)

OTHER PUBLICATIONS

Bichlmeier et al., "Contextual Anatomic Mimesis Hybrid In-Situ Visualization Method for Improving Multi-Sensory Depth Perception in Medical Augmented Reality", IEEE, 10 pages, 2007.
(Continued)

*Primary Examiner* — Javid A Amini

(57) ABSTRACT

An augmented reality surgical system includes a head mounted display (HMD) with a see-through display screen, a motion sensor, a camera, and computer equipment. The motion sensor outputs a head motion signal indicating measured movement of the HMD. The computer equipment computes the relative location and orientation of reference markers connected to the HMD and to the patient based on processing a video signal from the camera. The computer equipment generates a three dimensional anatomical model using patient data created by medical imaging equipment, and rotates and scales at least a portion of the three dimensional anatomical model based on the relative location and orientation of the reference markers, and further rotate at least a portion of the three dimensional anatomical model based on the head motion signal to track measured move-
(Continued)

ment of the HMD. The rotated and scaled three dimensional anatomical model is displayed on the display screen.

15 Claims, 20 Drawing Sheets

Related U.S. Application Data continuation of application No. 15/713,839, filed on Sep. 25, 2017, now Pat. No. 10,650,594, which is a continuation of application No. 15/013,594, filed on Feb. 2, 2016, now Pat. No. 10,013,808.

(60) Provisional application No. 62/270,895, filed on Dec. 22, 2015, provisional application No. 62/181,433, filed on Jun. 18, 2015, provisional application No. 62/111,379, filed on Feb. 3, 2015.

(51) Int. Cl.
  *G06F 3/0346* (2013.01)
  *A61B 90/00* (2016.01)
  *A61B 34/10* (2016.01)
  *G06T 19/20* (2011.01)

(52) U.S. Cl.
  CPC .............. *G06F 3/012* (2013.01); *G06F 3/017* (2013.01); *G06F 3/0346* (2013.01); *G06T 19/20* (2013.01); *A61B 2034/105* (2016.02); *A61B 2090/365* (2016.02); *A61B 2090/368* (2016.02); *A61B 2090/372* (2016.02); *G06T 2207/30204* (2013.01); *G06T 2210/41* (2013.01); *G06T 2219/2016* (2013.01)

(58) Field of Classification Search
  USPC ........................................................ 345/633
  See application file for complete search history.

(56) References Cited

U.S. PATENT DOCUMENTS

| | | |
|---|---|---|
| 5,246,010 A | 9/1993 | Gazzara et al. |
| 5,526,812 A | 6/1996 | Dumoulin et al. |
| 5,598,453 A | 1/1997 | Baba et al. |
| 5,740,802 A | 4/1998 | Nafis et al. |
| 5,772,594 A | 6/1998 | Barrick |
| 5,961,456 A | 10/1999 | Gildenberg |
| 5,987,960 A | 11/1999 | Messner et al. |
| 6,031,888 A | 2/2000 | Ivan et al. |
| 6,144,875 A | 11/2000 | Schweikard et al. |
| 6,203,196 B1 | 3/2001 | Meyer et al. |
| 6,226,548 B1 | 5/2001 | Foley et al. |
| 6,301,495 B1 | 10/2001 | Gueziec et al. |
| 6,306,126 B1 | 10/2001 | Montezuma |
| 6,314,311 B1 | 11/2001 | Williams et al. |
| 6,320,929 B1 | 11/2001 | Von Der Haar |
| 6,349,001 B1 | 2/2002 | Spitzer |
| 6,396,497 B1 | 5/2002 | Reichlen |
| 6,477,400 B1 | 11/2002 | Barrick |
| 6,484,049 B1 | 11/2002 | Seeley et al. |
| 6,487,267 B1 | 11/2002 | Wolter |
| 6,490,475 B1 | 12/2002 | Seeley et al. |
| 6,501,981 B1 | 12/2002 | Schweikard et al. |
| 6,503,195 B1 | 1/2003 | Keller et al. |
| 6,535,756 B1 | 3/2003 | Simon et al. |
| 6,544,176 B2 | 4/2003 | Mikus et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,666,579 B2 | 12/2003 | Jensen |
| 6,669,635 B2 | 12/2003 | Kessman et al. |
| 6,725,080 B2 | 4/2004 | Melkent et al. |
| 6,757,068 B2 | 6/2004 | Foxlin |
| 6,782,287 B2 | 8/2004 | Grzeszczuk |
| 6,856,324 B2 | 2/2005 | Sauer et al. |
| 6,856,826 B2 | 2/2005 | Seeley et al. |
| 6,856,827 B2 | 2/2005 | Seeley et al. |
| 6,867,753 B2 | 3/2005 | Chinthammit et al. |
| 6,919,867 B2 | 7/2005 | Sauer |
| 6,920,347 B2 | 7/2005 | Simon et al. |
| 6,922,632 B2 | 7/2005 | Foxlin |
| 6,947,786 B2 | 9/2005 | Simon et al. |
| 6,988,009 B2 | 1/2006 | Grimm et al. |
| 6,996,487 B2 | 2/2006 | Jutras et al. |
| 7,016,457 B1 | 3/2006 | Senzig et al. |
| 7,043,961 B2 | 5/2006 | Pandey et al. |
| 7,050,845 B2 | 5/2006 | Vilsmeier |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,176,936 B2 | 2/2007 | Sauer et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,301,648 B2 | 11/2007 | Foxlin |
| 7,313,430 B2 | 12/2007 | Urquhart et al. |
| 7,318,805 B2 | 1/2008 | Schweikard et al. |
| 7,324,623 B2 | 1/2008 | Heuscher et al. |
| 7,327,865 B2 | 2/2008 | Fu et al. |
| 7,460,637 B2 | 12/2008 | Clinthorne et al. |
| 7,480,402 B2 | 1/2009 | Bar-Zohar et al. |
| 7,493,153 B2 | 2/2009 | Ahmed et al. |
| 7,505,617 B2 | 3/2009 | Fu et al. |
| 7,542,791 B2 | 6/2009 | Mire et al. |
| 7,570,791 B2 | 8/2009 | Frank et al. |
| 7,599,730 B2 | 10/2009 | Hunter et al. |
| 7,605,826 B2 | 10/2009 | Sauer |
| 7,606,613 B2 | 10/2009 | Simon et al. |
| 7,623,902 B2 | 11/2009 | Pacheco |
| 7,643,862 B2 | 1/2010 | Schoenefeld |
| 7,661,881 B2 | 2/2010 | Gregerson et al. |
| 7,683,331 B2 | 3/2010 | Chang |
| 7,683,332 B2 | 3/2010 | Chang |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,725,253 B2 | 5/2010 | Foxlin |
| 7,726,171 B2 | 6/2010 | Langlotz et al. |
| 7,760,849 B2 | 7/2010 | Zhang |
| 7,774,044 B2 | 8/2010 | Sauer et al. |
| 7,796,728 B2 | 9/2010 | Bergfjord |
| 7,813,838 B2 | 10/2010 | Sommer |
| 7,831,294 B2 | 11/2010 | Mswanathan |
| 7,835,778 B2 | 11/2010 | Foley et al. |
| 7,835,784 B2 | 11/2010 | Mire et al. |
| 7,840,256 B2 | 11/2010 | Lakin et al. |
| 7,844,320 B2 | 11/2010 | Shahidi |
| 7,853,305 B2 | 12/2010 | Simon et al. |
| 7,853,313 B2 | 12/2010 | Thompson |
| 7,900,524 B2 | 3/2011 | Calloway et al. |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,987,001 B2 | 7/2011 | Teichman et al. |
| 8,019,045 B2 | 9/2011 | Kato |
| 8,021,310 B2 | 9/2011 | Sanborn et al. |
| 8,052,688 B2 | 11/2011 | Wolf, II |
| 8,086,299 B2 | 12/2011 | Adler et al. |
| 8,098,914 B2 | 1/2012 | Liao et al. |
| 8,100,950 B2 | 1/2012 | St. Clair et al. |
| 8,106,905 B2 | 1/2012 | Markowitz et al. |
| 8,116,430 B1 | 2/2012 | Shapiro et al. |
| 8,121,249 B2 | 2/2012 | Wang et al. |
| 8,123,675 B2 | 2/2012 | Funda et al. |
| 8,150,494 B2 | 4/2012 | Simon et al. |
| 8,208,708 B2 | 6/2012 | Homan et al. |

(56) References Cited

U.S. PATENT DOCUMENTS

| | | |
|---|---|---|
| 8,224,024 B2 | 7/2012 | Foxlin et al. |
| 8,228,368 B2 | 7/2012 | Zhao et al. |
| 8,311,611 B2 | 11/2012 | Csavoy et al. |
| 8,314,815 B2 | 11/2012 | Navab et al. |
| 8,325,873 B2 | 12/2012 | Helm et al. |
| 8,335,557 B2 | 12/2012 | Maschke |
| 8,358,818 B2 | 1/2013 | Miga et al. |
| 8,374,673 B2 | 2/2013 | Adcox et al. |
| 8,379,791 B2 | 2/2013 | Forthmann et al. |
| 8,386,019 B2 | 2/2013 | Camus et al. |
| 8,394,099 B2 | 3/2013 | Patwardhan |
| 8,427,527 B2 | 4/2013 | Visser et al. |
| 8,462,911 B2 | 6/2013 | Vesel et al. |
| 8,504,136 B1 | 8/2013 | Sun et al. |
| 8,509,503 B2 | 8/2013 | Nahum et al. |
| 8,526,700 B2 | 9/2013 | Isaacs |
| 8,532,741 B2 | 9/2013 | Heruth et al. |
| 8,541,970 B2 | 9/2013 | Nowlin et al. |
| 8,560,118 B2 | 10/2013 | Green et al. |
| 8,597,198 B2 | 12/2013 | Sanborn et al. |
| 8,611,985 B2 | 12/2013 | Lavallee et al. |
| 8,630,389 B2 | 1/2014 | Kato |
| 8,634,897 B2 | 1/2014 | Simon et al. |
| 8,660,635 B2 | 2/2014 | Simon et al. |
| 8,672,836 B2 | 3/2014 | Higgins et al. |
| 8,678,647 B2 | 3/2014 | Gregerson et al. |
| 8,696,458 B2 | 4/2014 | Foxlin et al. |
| 8,700,123 B2 | 4/2014 | Okamura et al. |
| 8,706,185 B2 | 4/2014 | Foley et al. |
| 8,727,618 B2 | 5/2014 | Maschke et al. |
| 8,738,115 B2 | 5/2014 | Amberg et al. |
| 8,740,882 B2 | 6/2014 | Jun et al. |
| 8,774,363 B2 | 7/2014 | Van Den Houten et al. |
| 8,781,186 B2 | 7/2014 | Clements et al. |
| 8,781,630 B2 | 7/2014 | Banks et al. |
| 8,784,443 B2 | 7/2014 | Tripathi |
| 8,787,520 B2 | 7/2014 | Baba |
| 8,792,704 B2 | 7/2014 | Isaacs |
| 8,798,231 B2 | 8/2014 | Notohara et al. |
| 8,812,077 B2 | 8/2014 | Dempsey |
| 8,814,793 B2 | 8/2014 | Brabrand |
| 8,818,105 B2 | 8/2014 | Myronenko et al. |
| 8,821,511 B2 | 9/2014 | Von Jako et al. |
| 8,842,893 B2 | 9/2014 | Teichman et al. |
| 8,867,703 B2 | 10/2014 | Shapiro et al. |
| 8,878,900 B2 | 11/2014 | Yang et al. |
| 8,888,821 B2 | 11/2014 | Rezach et al. |
| 8,891,847 B2 | 11/2014 | Helm et al. |
| 8,938,283 B2 | 1/2015 | Zentgraf et al. |
| 8,938,301 B2 | 1/2015 | Hagedorn |
| 8,945,140 B2 | 2/2015 | Hubschman et al. |
| 8,948,935 B1 | 2/2015 | Peeters |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,095,252 B2 | 8/2015 | Popovic |
| 9,105,207 B2 | 8/2015 | Leung |
| 9,107,683 B2 | 8/2015 | Hourtash et al. |
| 9,119,670 B2 | 9/2015 | Yang et al. |
| 9,123,155 B2 | 9/2015 | Cunningham et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,232,982 B2 | 1/2016 | Soler et al. |
| 9,265,468 B2 | 2/2016 | Rai et al. |
| 9,289,267 B2 | 3/2016 | Sauer et al. |
| 9,295,435 B2 | 3/2016 | Florent et al. |
| 9,308,050 B2 | 4/2016 | Kostrzewski et al. |
| 9,333,361 B2 | 5/2016 | Li et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,436,993 B1 | 9/2016 | Stolka et al. |
| 9,439,556 B2 | 9/2016 | Pandya et al. |
| 9,492,235 B2 | 11/2016 | Hourtash et al. |
| 9,492,241 B2 | 11/2016 | Jaskowicz et al. |
| 9,498,132 B2 | 11/2016 | Maier-Hein et al. |
| 9,538,962 B1 | 1/2017 | Hannaford et al. |
| 9,547,940 B1 | 1/2017 | Sun et al. |
| 9,554,866 B2 | 1/2017 | Cunningham et al. |
| 9,563,266 B2 | 2/2017 | Banerjee et al. |
| 9,576,106 B2 | 2/2017 | Ahmad |
| 9,592,096 B2 | 3/2017 | Maillet et al. |
| 9,626,805 B2 | 4/2017 | Lampotang et al. |
| 9,645,379 B2 | 5/2017 | Ren et al. |
| 9,681,925 B2 | 6/2017 | Azar et al. |
| 9,707,400 B2 | 7/2017 | Grenz et al. |
| 9,750,465 B2 | 9/2017 | Engel et al. |
| 9,757,203 B2 | 9/2017 | Hourtash et al. |
| 9,767,608 B2 | 9/2017 | Lee et al. |
| 9,773,312 B2 | 9/2017 | Lee |
| 9,788,756 B2 | 10/2017 | Demmer |
| 9,795,282 B2 | 10/2017 | Sholev et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,833,254 B1 | 12/2017 | Barral et al. |
| 9,835,862 B1 | 12/2017 | Zhou et al. |
| 9,839,365 B1 | 12/2017 | Homyk et al. |
| 9,848,922 B2 | 12/2017 | Tohmeh et al. |
| 9,855,103 B2 | 1/2018 | Tsekos et al. |
| 9,892,564 B1 | 2/2018 | Cvetko et al. |
| 9,895,063 B1 | 2/2018 | Hannaford et al. |
| 9,898,662 B2 | 2/2018 | Tsuda et al. |
| 9,911,187 B2 | 3/2018 | Steinle et al. |
| 9,925,011 B2 | 3/2018 | Gombert et al. |
| 9,925,013 B2 | 3/2018 | Dell et al. |
| 9,928,629 B2 | 3/2018 | Benishti et al. |
| 9,931,025 B1 | 4/2018 | Graetzel et al. |
| 9,931,040 B2 | 4/2018 | Homyk et al. |
| 9,949,637 B1 | 4/2018 | Wong et al. |
| 9,970,955 B1 | 5/2018 | Homyk et al. |
| 9,980,698 B2 | 5/2018 | Bakker et al. |
| 10,010,373 B2 | 7/2018 | Canfield et al. |
| 10,010,379 B1 | 7/2018 | Gibby et al. |
| 10,013,808 B2 | 7/2018 | Jones et al. |
| 10,016,243 B2 | 7/2018 | Esterberg |
| 10,034,717 B2 | 7/2018 | Miller et al. |
| 10,052,170 B2 | 8/2018 | Saget et al. |
| 10,073,515 B2 | 9/2018 | Awdeh |
| 10,092,164 B2 | 10/2018 | Sholev et al. |
| 10,092,237 B2 | 10/2018 | Wong et al. |
| 10,092,361 B2 | 10/2018 | Ferro et al. |
| 10,105,187 B2 | 10/2018 | Corndorf et al. |
| 10,152,789 B2 | 12/2018 | Carnes et al. |
| 10,152,796 B2 | 12/2018 | Guo et al. |
| 10,154,239 B2 | 12/2018 | Casas |
| 10,163,252 B2 | 12/2018 | Yun et al. |
| 10,166,019 B2 | 1/2019 | Nawana et al. |
| 10,176,642 B2 | 1/2019 | Tran et al. |
| 10,191,615 B2 | 1/2019 | Helm et al. |
| 10,194,990 B2 | 2/2019 | Amanatullah et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,226,298 B2 | 3/2019 | Ourselin et al. |
| 10,231,784 B2 | 3/2019 | Hettrick et al. |
| 10,235,737 B2 | 3/2019 | Cheatham, III et al. |
| 10,242,292 B2 | 3/2019 | Zisimopoulos et al. |
| 10,251,714 B2 | 4/2019 | Carnes et al. |
| 10,258,426 B2 | 4/2019 | Silva et al. |
| 10,265,138 B2 | 4/2019 | Choudhry et al. |
| 10,275,927 B2 | 4/2019 | Kuhn et al. |
| 10,278,726 B2 | 5/2019 | Barth et al. |
| 10,285,765 B2 | 5/2019 | Sachs et al. |
| 10,292,780 B2 | 5/2019 | Park |
| 10,360,730 B2 | 7/2019 | Hasegwa |

(56) References Cited

U.S. PATENT DOCUMENTS

| | | |
|---|---|---|
| 10,366,489 B2 | 7/2019 | Boettger et al. |
| 10,376,318 B2 | 8/2019 | Tsusaka et al. |
| 10,379,048 B2 | 8/2019 | Wang et al. |
| 10,383,654 B2 | 8/2019 | Yilmaz et al. |
| 10,390,780 B2 | 8/2019 | Han et al. |
| 10,390,890 B2 | 8/2019 | Jagga |
| 10,390,891 B2 | 8/2019 | Govari et al. |
| 10,398,514 B2 | 9/2019 | Ryan et al. |
| 10,405,927 B1 | 9/2019 | Lang |
| 10,412,377 B2 | 9/2019 | Forthmann et al. |
| 10,413,363 B2 | 9/2019 | Fahim et al. |
| 10,426,339 B2 | 10/2019 | Papac |
| 10,426,345 B2 | 10/2019 | Shekhar et al. |
| 10,426,554 B2 | 10/2019 | Siewerdsen et al. |
| 10,431,008 B2 | 10/2019 | Djajadiningrat et al. |
| 10,432,913 B2 | 10/2019 | Shokri et al. |
| 10,433,915 B2 | 10/2019 | Isaacs et al. |
| 10,448,003 B2 | 10/2019 | Gafenberg |
| 10,546,423 B2 * | 1/2020 | Jones .................. G06T 19/006 |
| 10,580,217 B2 * | 3/2020 | Jones .................... A61B 34/20 |
| 10,650,594 B2 * | 5/2020 | Jones .................... G06F 3/012 |
| 11,062,522 B2 * | 7/2021 | Jones .................... G06F 3/011 |
| 11,176,750 B2 * | 11/2021 | Jones .................. G06T 19/20 |
| 11,217,028 B2 * | 1/2022 | Jones .................... A61B 34/10 |
| 11,461,983 B2 * | 10/2022 | Jones .................. G06F 3/0346 |
| 2001/0036302 A1 | 11/2001 | Miller |
| 2003/0179308 A1 | 9/2003 | Zamorano et al. |
| 2003/0210812 A1 | 11/2003 | Khamene et al. |
| 2004/0076259 A1 | 4/2004 | Jensen et al. |
| 2004/0254454 A1 | 12/2004 | Kockro |
| 2005/0054910 A1 | 3/2005 | Tremblay et al. |
| 2005/0215879 A1 | 9/2005 | Chuanggui |
| 2006/0176242 A1 | 8/2006 | Jaramaz et al. |
| 2006/0184396 A1 | 8/2006 | Dennis et al. |
| 2006/0291612 A1 | 12/2006 | Nishide et al. |
| 2006/0293557 A1 | 12/2006 | Chuanggui et al. |
| 2007/0021738 A1 | 1/2007 | Hasset et al. |
| 2007/0038059 A1 | 2/2007 | Sheffer et al. |
| 2007/0073133 A1 | 3/2007 | Schoenefeld |
| 2007/0167702 A1 | 7/2007 | Hasser et al. |
| 2007/0236514 A1 | 10/2007 | Agusanto et al. |
| 2007/0238981 A1 | 10/2007 | Zhu et al. |
| 2007/0248261 A1 | 10/2007 | Zhou et al. |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | von Jako |
| 2008/0123910 A1 | 5/2008 | Zhu |
| 2008/0144906 A1 | 6/2008 | Allred et al. |
| 2008/0161680 A1 | 7/2008 | von Jako et al. |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0235052 A1 | 9/2008 | Node-Langlois et al. |
| 2008/0243142 A1 | 10/2008 | Gildenberg |
| 2008/0269596 A1 | 10/2008 | Revie et al. |
| 2008/0287781 A1 | 11/2008 | Revie et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0185655 A1 | 7/2009 | Koken et al. |
| 2009/0198121 A1 | 8/2009 | Hoheisel |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0210902 A1 | 8/2010 | Navab et al. |
| 2010/0228117 A1 | 9/2010 | Hartmann |
| 2010/0274120 A1 | 10/2010 | Heuscher |
| 2011/0098553 A1 | 4/2011 | Robbins et al. |
| 2011/0282189 A1 | 11/2011 | Graumann |
| 2011/0286573 A1 | 11/2011 | Schretter et al. |
| 2011/0306986 A1 | 12/2011 | Lee et al. |
| 2012/0035507 A1 | 2/2012 | George et al. |
| 2012/0051498 A1 | 3/2012 | Koishi |
| 2012/0059378 A1 | 3/2012 | Farrell |
| 2012/0143084 A1 | 6/2012 | Shoham |
| 2012/0203067 A1 | 8/2012 | Higgins et al. |
| 2012/0226145 A1 | 9/2012 | Chang et al. |
| 2012/0235909 A1 | 9/2012 | Birkenbach et al. |
| 2012/0294498 A1 | 11/2012 | Popovic |
| 2012/0302875 A1 | 11/2012 | Kohring |
| 2013/0016889 A1 | 1/2013 | Myronenko et al. |
| 2013/0060146 A1 | 3/2013 | Yang et al. |
| 2013/0094742 A1 | 4/2013 | Feilkas |
| 2013/0113791 A1 | 5/2013 | Isaacs et al. |
| 2013/0165937 A1 | 6/2013 | Patwardhan |
| 2013/0211232 A1 | 8/2013 | Murphy et al. |
| 2013/0267838 A1 | 10/2013 | Fronk et al. |
| 2013/0274596 A1 | 10/2013 | Azizian et al. |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345757 A1 | 12/2013 | Stad |
| 2014/0022283 A1 | 1/2014 | Chan et al. |
| 2014/0044333 A1 | 2/2014 | Barth, Jr. et al. |
| 2014/0046132 A1 | 2/2014 | Hoeg et al. |
| 2014/0049629 A1 | 2/2014 | Siewerdsen et al. |
| 2014/0080086 A1 | 3/2014 | Chen |
| 2014/0085203 A1 | 3/2014 | Kobayashi |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0139405 A1 | 5/2014 | Ribble et al. |
| 2014/0206994 A1 | 7/2014 | Jain et al. |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0347353 A1 | 11/2014 | Popovic et al. |
| 2014/0371577 A1 | 12/2014 | Maillet et al. |
| 2015/0031990 A1 | 1/2015 | Boctor et al. |
| 2015/0039034 A1 | 2/2015 | Frankel et al. |
| 2015/0073265 A1 | 3/2015 | Popovic et al. |
| 2015/0084990 A1 | 3/2015 | Laor |
| 2015/0085970 A1 | 3/2015 | Bouhnik et al. |
| 2015/0112126 A1 | 4/2015 | Popovic et al. |
| 2015/0146847 A1 | 5/2015 | Liu |
| 2015/0146946 A1 | 5/2015 | Elhawary et al. |
| 2015/0150524 A1 | 6/2015 | Yorkston et al. |
| 2015/0196261 A1 | 7/2015 | Funk |
| 2015/0201892 A1 | 7/2015 | Hummel et al. |
| 2015/0213633 A1 | 7/2015 | Chang et al. |
| 2015/0230689 A1 | 8/2015 | Blohm et al. |
| 2015/0238276 A1 | 8/2015 | Atarot et al. |
| 2015/0248793 A1 | 9/2015 | Abovitz et al. |
| 2015/0305828 A1 | 10/2015 | Park et al. |
| 2015/0335480 A1 | 11/2015 | Alvarez et al. |
| 2015/0342647 A1 | 12/2015 | Frankel et al. |
| 2015/0366628 A1 | 12/2015 | Ingmanson |
| 2016/0005194 A1 | 1/2016 | Schretter et al. |
| 2016/0015469 A1 | 1/2016 | Goshayesh et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0019715 A1 | 1/2016 | Haddick et al. |
| 2016/0019716 A1 | 1/2016 | Huang et al. |
| 2016/0019719 A1 | 1/2016 | Osterhout et al. |
| 2016/0021304 A1 | 1/2016 | Osterhout |
| 2016/0022125 A1 | 1/2016 | Nicolau et al. |
| 2016/0086380 A1 | 3/2016 | Vayser et al. |
| 2016/0163105 A1 | 6/2016 | Hong et al. |
| 2016/0166329 A1 | 6/2016 | Langan et al. |
| 2016/0235480 A1 | 8/2016 | Scholl et al. |
| 2016/0249989 A1 | 9/2016 | Devam et al. |
| 2016/0249990 A1 | 9/2016 | Glozman et al. |
| 2016/0287337 A1 | 10/2016 | Aram et al. |
| 2016/0302871 A1 | 10/2016 | Gregerson et al. |
| 2016/0317119 A1 | 11/2016 | Tahmasebi Maraghoosh et al. |
| 2016/0320322 A1 | 11/2016 | Suzuki |
| 2016/0324598 A1 | 11/2016 | Bothorel et al. |
| 2016/0331335 A1 | 11/2016 | Gregerson et al. |
| 2016/0360117 A1 | 12/2016 | Elefteriu et al. |
| 2017/0035517 A1 | 2/2017 | Geri et al. |

(56) References Cited

U.S. PATENT DOCUMENTS

| | | |
|---|---|---|
| 2017/0053437 A1 | 2/2017 | Ye et al. |
| 2017/0099479 A1 | 4/2017 | Browd et al. |
| 2017/0119471 A1 | 5/2017 | Winner et al. |
| 2017/0119474 A1 | 5/2017 | Kronman |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0151034 A1 | 6/2017 | Oda et al. |
| 2017/0156816 A1 | 6/2017 | Ibrahim |
| 2017/0172381 A1 | 6/2017 | Morimoto |
| 2017/0172663 A1 | 6/2017 | Popovic et al. |
| 2017/0202624 A1 | 7/2017 | Atarot et al. |
| 2017/0202629 A1 | 7/2017 | Maillet et al. |
| 2017/0202633 A1 | 7/2017 | Liu |
| 2017/0212723 A1 | 7/2017 | Marot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224427 A1 | 8/2017 | Lavallee et al. |
| 2017/0231710 A1 | 8/2017 | Scholl et al. |
| 2017/0231714 A1 | 8/2017 | Kosmecki et al. |
| 2017/0251900 A1 | 9/2017 | Hansen et al. |
| 2017/0256095 A1 | 9/2017 | Bani-Hashemi |
| 2017/0258426 A1 | 9/2017 | Risher-Kelly et al. |
| 2017/0273549 A1 | 9/2017 | Nazareth et al. |
| 2017/0273748 A1 | 9/2017 | Hourtash et al. |
| 2017/0296277 A1 | 10/2017 | Hourtash et al. |
| 2017/0296292 A1 | 10/2017 | Mahmood et al. |
| 2017/0315364 A1 | 11/2017 | Masumoto |
| 2017/0322410 A1 | 11/2017 | Watson et al. |
| 2017/0323062 A1 | 11/2017 | Djajadiningrat et al. |
| 2017/0336870 A1 | 11/2017 | Everett et al. |
| 2017/0360493 A1 | 12/2017 | Zucher et al. |
| 2017/0367766 A1 | 12/2017 | Mahfouz |
| 2017/0367771 A1 | 12/2017 | Tako et al. |
| 2018/0021099 A1 | 1/2018 | Warner et al. |
| 2018/0032130 A1 | 2/2018 | Meglan |
| 2018/0042692 A1 | 2/2018 | Kim et al. |
| 2018/0049809 A1 | 2/2018 | Marti et al. |
| 2018/0071032 A1 | 3/2018 | De Almeida Barreto |
| 2018/0078316 A1 | 3/2018 | Schaewe et al. |
| 2018/0082480 A1 | 3/2018 | White et al. |
| 2018/0092698 A1 | 4/2018 | Chopra et al. |
| 2018/0092706 A1 | 4/2018 | Anderson et al. |
| 2018/0116724 A1 | 5/2018 | Gmeiner et al. |
| 2018/0116732 A1 | 5/2018 | Lin et al. |
| 2018/0125586 A1 | 5/2018 | Sela et al. |
| 2018/0140362 A1 | 5/2018 | Cali et al. |
| 2018/0158201 A1 | 6/2018 | Thompson et al. |
| 2018/0161102 A1 | 6/2018 | Wei et al. |
| 2018/0168730 A1 | 6/2018 | Nazy |
| 2018/0168741 A1 | 6/2018 | Swayze et al. |
| 2018/0168769 A1 | 6/2018 | Wood et al. |
| 2018/0185100 A1 | 7/2018 | Weinstein et al. |
| 2018/0220100 A1 | 8/2018 | Ovchinnikov et al. |
| 2018/0228555 A1 | 8/2018 | Charron et al. |
| 2018/0232925 A1 | 8/2018 | Frakes et al. |
| 2018/0233222 A1 | 8/2018 | Daley et al. |
| 2018/0235739 A1 | 8/2018 | Jahn |
| 2018/0247449 A1 | 8/2018 | Park et al. |
| 2018/0249912 A1 | 9/2018 | Schneider et al. |
| 2018/0256256 A1 | 9/2018 | May et al. |
| 2018/0263698 A1 | 9/2018 | Wang et al. |
| 2018/0263727 A1 | 9/2018 | Pellerito |
| 2018/0289428 A1 | 10/2018 | Lee et al. |
| 2018/0289983 A1 | 10/2018 | Fishman |
| 2018/0299675 A1 | 10/2018 | Benz et al. |
| 2018/0303377 A1 | 10/2018 | West et al. |
| 2018/0303558 A1 | 10/2018 | Thomas |
| 2018/0303667 A1 | 10/2018 | Peyman |
| 2018/0310811 A1 | 11/2018 | Meglan et al. |
| 2018/0310831 A1 | 11/2018 | Cheng et al. |
| 2018/0310875 A1 | 11/2018 | Meglan et al. |
| 2018/0325604 A1 | 11/2018 | Atarot et al. |
| 2018/0325618 A1 | 11/2018 | Justin et al. |
| 2018/0333073 A1 | 11/2018 | Hill et al. |
| 2018/0333207 A1 | 11/2018 | Barrera |
| 2018/0333208 A1 | 11/2018 | Kotian et al. |
| 2018/0344266 A1 | 12/2018 | Altmann |
| 2018/0344408 A1 | 12/2018 | Rotilio et al. |
| 2018/0357825 A1 | 12/2018 | Hoffmann et al. |
| 2018/0360310 A1 | 12/2018 | Berlin |
| 2018/0368930 A1 | 12/2018 | Esterberg et al. |
| 2019/0000564 A1 | 1/2019 | Navab et al. |
| 2019/0000570 A1 | 1/2019 | Esterberg et al. |
| 2019/0008592 A1 | 1/2019 | Thienphrapa et al. |
| 2019/0011709 A1 | 1/2019 | Yadav et al. |
| 2019/0015162 A1 | 1/2019 | Abhari et al. |
| 2019/0015167 A1 | 1/2019 | Draelos et al. |
| 2019/0029757 A1 | 1/2019 | Roh et al. |
| 2019/0035156 A1 | 1/2019 | Wei et al. |
| 2019/0038362 A1 | 2/2019 | Nash et al. |
| 2019/0046276 A1 | 2/2019 | Inglese et al. |
| 2019/0050665 A1 | 2/2019 | Sakuragi |
| 2019/0053851 A1 | 2/2019 | Sieminonow et al. |
| 2019/0053855 A1 | 2/2019 | Siemionow et al. |
| 2019/0053858 A1 | 2/2019 | Kapoo et al. |
| 2019/0054632 A1 | 2/2019 | Grafenberg et al. |
| 2019/0059773 A1 | 2/2019 | Laughlin et al. |
| 2019/0066260 A1 | 2/2019 | Suehling et al. |
| 2019/0066390 A1 | 2/2019 | Vogel et al. |
| 2019/0069962 A1 | 3/2019 | Tabandeh et al. |
| 2019/0076194 A1 | 3/2019 | Jang |
| 2019/0080515 A1 | 3/2019 | Geri et al. |
| 2019/0088162 A1 | 3/2019 | Meglan |
| 2019/0090955 A1 | 3/2019 | Singh et al. |
| 2019/0099221 A1 | 4/2019 | Schmidt et al. |
| 2019/0104919 A1 | 4/2019 | Shelton, IV et al. |
| 2019/0108654 A1 | 4/2019 | Lasserre et al. |
| 2019/0117190 A1 | 4/2019 | Djajadonongrat |
| 2019/0122443 A1 | 4/2019 | Stocker |
| 2019/0125361 A1 | 5/2019 | Shelton, IV et al. |
| 2019/0125454 A1 | 5/2019 | Shelton, IV et al. |
| 2019/0142520 A1 | 5/2019 | Vandyken |
| 2019/0159841 A1 | 5/2019 | Abhari et al. |
| 2019/0167148 A1 | 6/2019 | Durfee et al. |
| 2019/0175058 A1 | 6/2019 | Godwin et al. |
| 2019/0180441 A1 | 6/2019 | Peng et al. |
| 2019/0183576 A1 | 6/2019 | Fahim et al. |
| 2019/0183590 A1 | 6/2019 | Hladio et al. |
| 2019/0192230 A1 | 6/2019 | Siemionow et al. |
| 2019/0192232 A1 | 6/2019 | Altmann et al. |
| 2019/0200844 A1 | 7/2019 | Shelton, IV et al. |
| 2019/0200977 A1 | 7/2019 | Shelton, IV et al. |
| 2019/0201104 A1 | 7/2019 | Shelton, IV et al. |
| 2019/0201106 A1 | 7/2019 | Siemionow et al. |
| 2019/0201158 A1 | 7/2019 | Shelton, IV et al. |
| 2019/0206062 A1 | 7/2019 | Matsuoka et al. |
| 2019/0206134 A1 | 7/2019 | Devam et al. |
| 2019/0206565 A1 | 7/2019 | Shelton, IV |
| 2019/0209241 A1 | 7/2019 | Begg |
| 2019/0214126 A1 | 7/2019 | Goetz |
| 2019/0216572 A1 | 7/2019 | Wang et al. |
| 2019/0223746 A1 | 7/2019 | Intrator |
| 2019/0231220 A1 | 8/2019 | Refai et al. |
| 2019/0231443 A1 | 8/2019 | McGinley et al. |
| 2019/0239850 A1 | 8/2019 | Dalvin et al. |
| 2019/0254753 A1 | 8/2019 | Johnson et al. |
| 2019/0274762 A1 | 9/2019 | Kim et al. |
| 2019/0282099 A1 | 9/2019 | Themelis |
| 2019/0307516 A1 | 10/2019 | Schotzko et al. |

OTHER PUBLICATIONS

Nicolau et al., "Augmented reality in laparoscopic surgical oncology", Surgical Oncology, 20, pp. 189-201, 2011.

\* cited by examiner

SURGEON HEAD-MOUNTED DISPLAY APPARATUSES

RELATED APPLICATIONS

The present patent application is a continuation of U.S. patent application Ser. No. 16/842,839 filed on Apr. 8, 2020 (published as U.S. Pat. Pub. No. 2020-0242845), which is a continuation of U.S. patent application Ser. No. 15/713,839 filed on Sep. 25, 2017 (now U.S. Pat. No. 10,650,594), which is a continuation of U.S. patent application Ser. No. 15/013,594 filed on Feb. 2, 2016 (now U.S. Pat. No. 10,013,808), which claims the benefit of priority from U.S. Provisional Patent Application No. 62/111,379 filed on Feb. 3, 2015, from U.S. Provisional Patent Application No. 62/181,433, filed on Jun. 18, 2015, and from U.S. Provisional Patent Application No. 62/270,895, filed on Dec. 22, 2015, the disclosure and content of all of which are incorporated by reference herein in their entireties.

TECHNICAL HELD

The present disclosure relates to surgical operating room equipment and procedures and, more particular, to generating anatomical models and other information to be displayed as augmenting reality in surgical operating rooms.

BACKGROUND

It has become commonplace in operating rooms (ORs) for surgeons and other personnel to refer to many different types of visual patient data during surgical procedures. For example, a surgeon may refer to digital photographs and video from magnetic resonance imaging equipment, computed tomography scanning equipment, x-ray equipment, three-dimensional ultrasound equipment, endoscopic equipment, 3D computer modeling equipment, patient monitoring equipment, medical records databases, and other equipment during a surgical procedure.

ORs therefore typically include many display devices positioned at various locations that are expected to be viewable during a procedure. Personnel may refer to display devices hung from a ceiling, mounted from a wall, supported on a cart, etc. However, it is difficult or not possible to position the display devices for convenient viewing by all necessary personnel. Mentally translating between the orientation of information shown on display devices that are angularly offset from the orientation of a patient's body can be particularly difficult, prone to errors, or inefficiently time-consuming for personnel during a procedure. Moreover, frequent shifting of focal reference from a patient surgical site to remotely located display devices may result in fatigue and have a deleterious effect on quality of the procedure.

Another difficulty surgeons and other personnel have is relating what is viewed on the display devices to precise locations on a patient. For example, it can be difficult for a surgeon to identify where a particular location within a displayed x-ray or other image corresponds to on the patient. Moreover, a surgeon may use a 3D anatomical model to practice before a procedure, but may not be able to effectively use the model during surgery because of the inherent difficulty of relating the model to the patient in real-time.

SUMMARY

Some embodiments of the present disclosure are directed to an augmented reality surgical system that includes a head mounted display, a motion sensor, at least one camera, and computer equipment. The head mounted display includes a see-through display screen that display images while allowing transmission of ambient light therethrough. The motion sensor is connected to the head mounted display and configured to output a head motion signal indicating measured movement of the head mounted display. The at least one camera is configured to Observe reference markers connected to the head mounted display, reference markers connected to a patient, and reference markers connected to a surgical tool located within a surgical room. The computer equipment is configured to compute the relative location and orientation a the reference markers connected to the head mounted display and the reference markers connected to the patient based on processing, a video signal from the at least one camera. The computer equipment is further configured to generate a three dimensional anatomical model using patient data created by medical imaging equipment that has imaged a portion of the patient, and to rotate and scale at least a portion of the three dimensional anatomical model based on the relative location and orientation of the reference markers connected to the head mounted display and the reference markers connected to the patient, and further rotate the at least a portion of the three dimensional anatomical model based on the head motion signal to track measured movement of the head mounted display. The computer equipment is further configured to generate a video signal based on the rotated and scaled three dimensional anatomical model, and to output the video signal to the display screen of the head mounted display.

Some other embodiments of the present disclosure are directed to an augmented reality surgical system for displaying multiple video streams to a user. The augmented reality surgical system includes a head mounted display, a motion sensor, and computer equipment. The head mounted display includes a see-through display screen that display images while allowing transmission of ambient light therethrough. The motion sensor is connected to the head mounted display and configured to output a head motion signal indicating measured movement of the head mounted display. The computer equipment is configured to receive a plurality of video streams from one or more source devices and to control which of the video streams are output as a video signal to the display screen based on the head motion signal.

Other systems, methods, and computer program products according to embodiments of the inventive subject matter will be or become apparent to one with skin in the art upon review of the following drawings and detailed description. It is intended that all such additional systems methods, and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

In the following detailed description, numerous specific details are set forth in order to provide a thorough understanding of embodiments of the present disclosure. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

Embodiments of the present disclosure are directed to an augmented reality surgical system that includes a head mounted display (HMD) apparatus that can be worn by a surgeon, physician, or other personnel during a medical procedure. The HMD can be configured to provide localized, real-time situational awareness to the wearer. The HMD includes a display screen that can be positioned within the line-of-sight and/or periphery Field Of View (FOV) of the wearer to provide visual information that can be organized and displayed as a single virtual display or as a collection of virtual displays that a wearer can navigate between to view using head movement, hand gestures, voice commands, eye control, and/or other operations disclosed herein.

A surgeon or other person can wear the MID to see a graphical representation of what is within the patient's body but covered from view by skin, muscle, organs, skeletal structure, etc. Using the MID can enable a surgeon to minimize the size of an incision by observing where the incision needs to be made to reveal a targeted portion of the body. Similarly, the HMD can be used when replacing a bone with prosthesis to enable a surgeon to observe an exact positioning reference that aids with orienting, and moving surgical tools and the prosthesis during the procedure. The HMD may operate to improve the efficiency, productivity, throughput, and/or accuracy, and/or safety of the wearer's performance of a medical procedure. Moreover, the MID can reduce mental fatigue by reducing or eliminating a need for the wearer to reference remote display devices having substantial angular offsets during a medical procedure.

Although various embodiments of systems having HMDs are described for use in the environment of a surgical operating room, they may be used in other applications. For example, the systems may be used within industrial environments such as warehousing applications, manufacturing applications, product inspection applications, and/or maintenance applications.

Example Head Mounted Display Apparatuses

Figure 1:
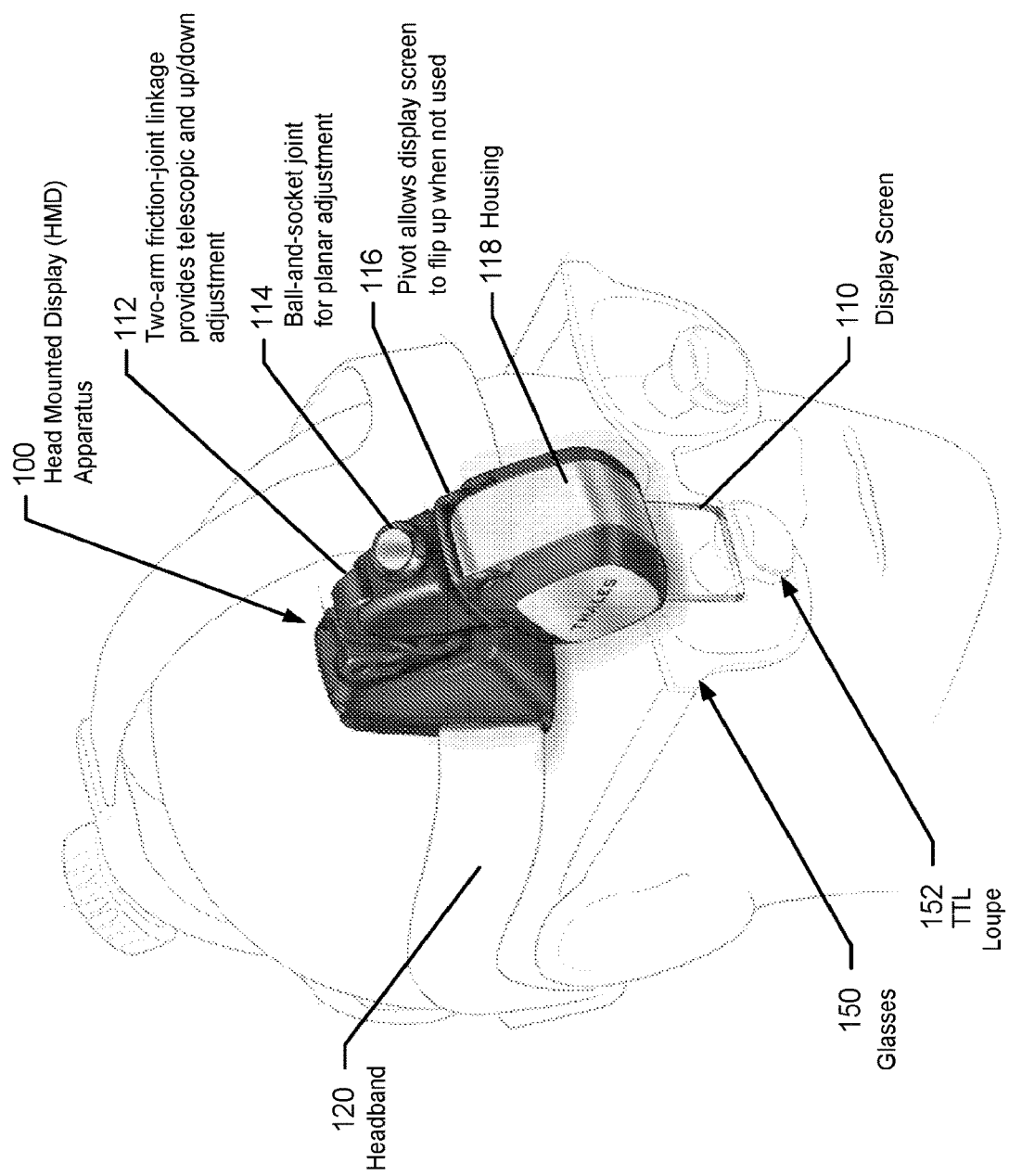
FIGS. 1-8 illustrate a head mounted display apparatus that can be worn on a user's head and operates according to some embodiments of the present disclosure.

FIG. 1 illustrates a HMD apparatus 100 (also "HMD 100" for brevity) configured according to some embodiments of the present disclosure. Referring to FIG. 1, the HMD 100 includes a semitransparent display screen 110 connected to a display module that processes and displays video and other images on the display screen 110 (e.g., a LCD display, a reflective screen on which the display module projects images, etc.) for viewing by a user. The display module may be within a housing 118 of the HMD 100 or may be contained within a communicatively connected computer system.

In the illustrated embodiment, the HMD 100 is mounted to a headband 120 and positioned so that the display screen 110 extends within the peripheral vision of the user. The housing 118 encloses electronic components that display information on the display screen 110 and may operate in combination with a remote but communicatively connected computer equipment and/or with computer equipment integrated within the housing 118 to sense and interpret movement of the head, sense and interpret gestures made by a user's hands or other objects, and/or sense and interpret voice commands by the user. The display screen 110 can provide a monocular see-through display or a stereo set of see-through displays so that the user can view information displayed on the display while looking through the display to view other objects. The headband 120 may include a headlamp, camera, or other apparatus that can be worn on a user's head.

The user is illustrated as wearing glasses 150 that include through-the-lens (TTL) loupes 152, protruding from lenses of the glasses 150, that provide magnified viewing to the user. The display screen 110 extends downward from the housing 118 and is positionable by the user to be in the user's field-of-view or immediately adjacent to the TTL loupes 152 within the user's peripheral vision. The display screen 110 can be a see-through display device allowing the user to see video superimposed on the environment seen through the display screen 110.

The TTL loupes 152 may not be included in the HMD 100 when the display screen 110 is configured to be in the direct line-of-sight of the user. Alternatively, the display screen 110 can be positioned adjacent to the TTL loupes 152 so that the user can make a minor upward shift in eye line-of-sight from looking through the TTL loupes 152 to instead view information displayed on the display screen 110. In some embodiments the display screen 110 may be incorporated within one or both TTL loupes 152 so that the user can look through the TTL loupes 152 to view graphical images super-imposed on objects within the FOV of the TTL loupe 152. The HMD 100 may be configured to be attachable to any type of eyeglass frames, including prescription glasses, protective glasses, frames without lenses, transparent or protective shields, etc.

The display screen 110 can be moved by a user to a location providing convenient visual reference through a two-arm friction joint linkage 112 that provides telescopic and up-and-down adjustment of location of the housing 118. A ball-and-socket joint 114 is connected between the linkage 112 and the housing 118 to provide planar adjustment for the display screen 110. A pivot joint 116 connected between the ball-and-socket joint 114 and the housing 118 allows the user to pivot the housing 118 and connected display screen 110. The display screen 110 can thereby be flipped-tip outside the user's peripheral vision when not being used.

The HMD 100 may include sensors such as inertial sensors or other sensors, such as a gyroscope, accelerometer (e.g., a multi-axis accelerometer), and/or magnetometer that output a signal indicating a measurement of movement or static orientation of the user's head while wearing the HMD 100. For example, the motion sensor may output a head motion signal that indicates yaw (i.e., rotation of the user's head left or right), pitch (i.e., rotation of the user's head up or down), and/or roll (i.e., side-to-side tilt of the user's head). The sensors may be spaced apart on the headband 120 or enclosed within the housing 118.

The HMD 100 may include at least one camera facing away from the user that outputs video and/or other images for processing and relay to other HMDs 100 worn by other personnel assisting with the procedure, to other display devices, and/or to a video server for storage. For example, the camera may be configured to be aligned with the user's line-of-sight when the user has adjusted the display screen 110 to be comfortably viewed by the user. When more than one camera is connected to the HMD 100, video streams from the cameras can be provided to an operational function that estimates distance to an object viewed by the cameras. The operational function can include triangulation of distance to the object based on angular offset of the object viewed in the video streams and a known distance between the cameras.

The at least one camera may be connected to a gesture interpretation module configured to sense gestures made by a user's hands or other objects, recognize a gesture as corresponding to one of a plurality of defined commands, and trigger operation of the command. The HMD 100 may include a microphone connected to a voice interpretation module configured to recognize a received voice command as corresponding to one of a plurality of defined voice commands, and trigger operation of the command.

The headband 120 may have a plurality of attachment points where inertial sensors, camera, microphone, etc. can be releasably attached. Some of the attachment points may have rigid supporting structures between them to maintain a defined physical alignment between the attached inertial sensors, etc.

Figure 2:
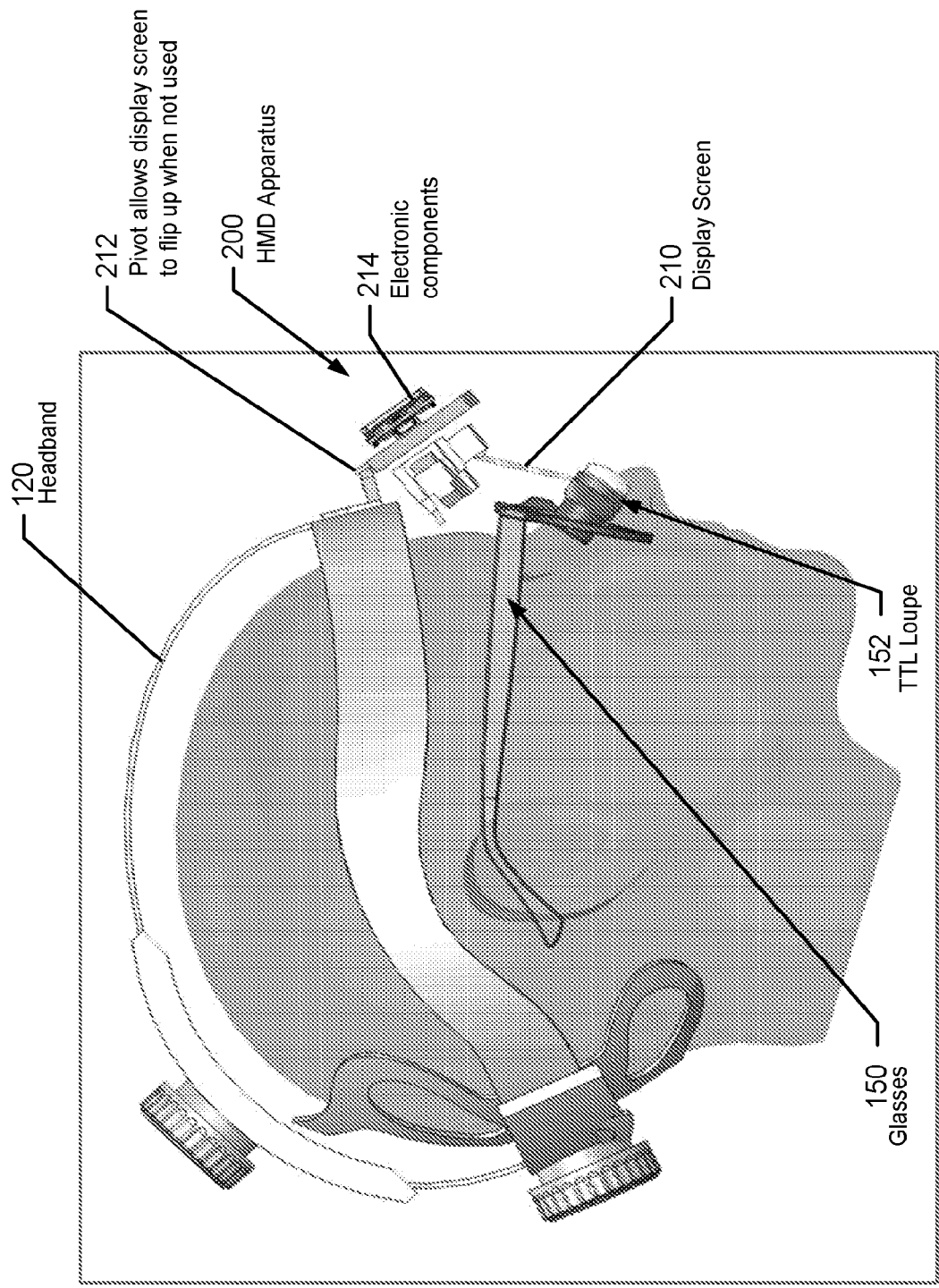

FIG. 2 illustrates a side view of another HMD 200 with a display screen 210 and electronic components 214 (shown without a housing) which are configured according to some embodiments of the present disclosure. The display screen 210 extends downward from the electronic components 214 to be in the user's line-of-sight or immediately adjacent TTL loupes 152 within the user's peripheral vision. The electronic components 214 are connected to the headband 120 via a pivot 212 allowing the electronic components 214 and connected display screen 210 to be flipped-down to a deployed position as shown in FIG. 2 and flipped-up to a stored position when the user does not desire to view the display screen 210.

Figure 3:
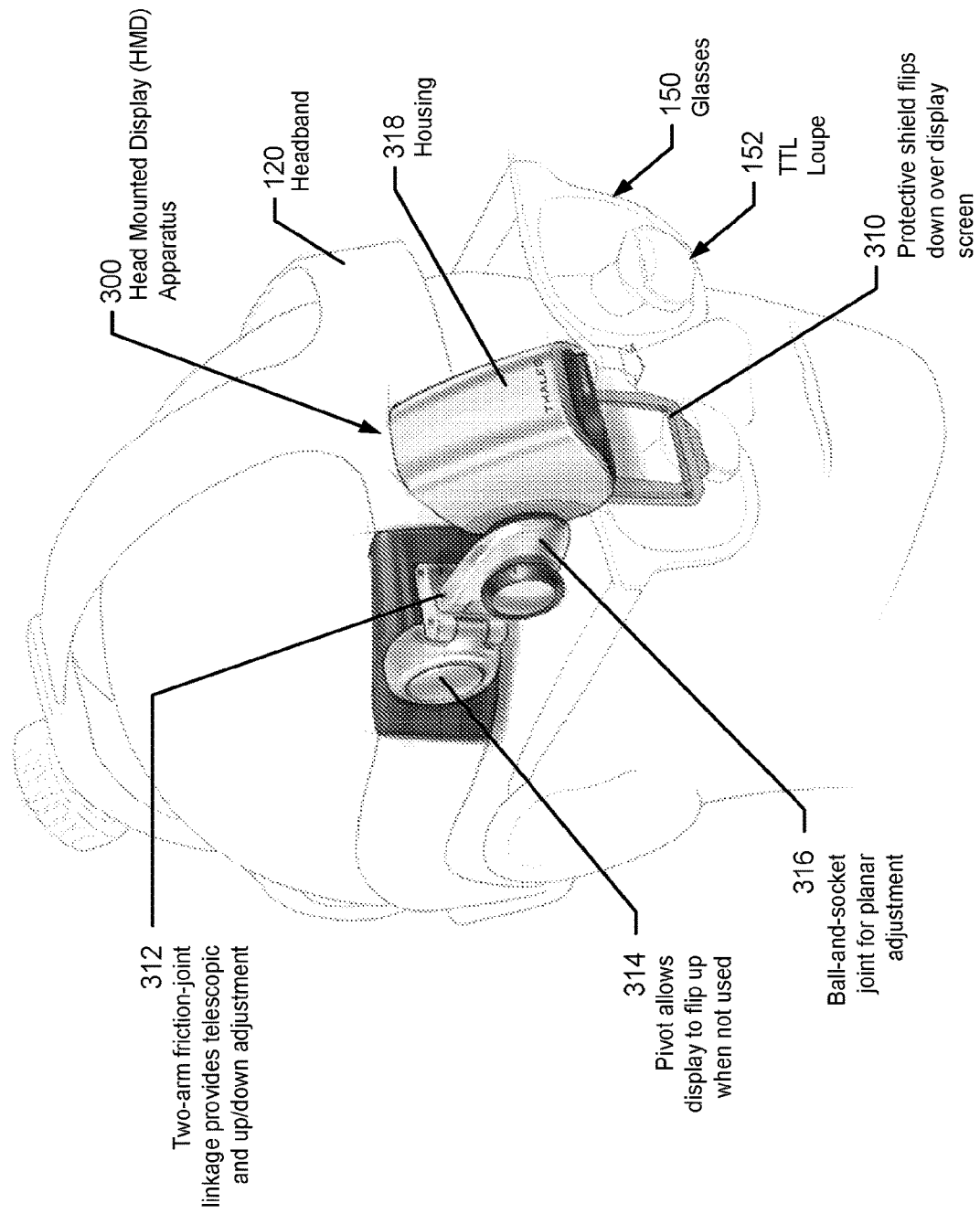

FIG. 3 illustrates another HMD 300 configured according to some embodiments of the present disclosure. The MID 300 includes a display screen illustrated behind a protective shield 310 that extends downward from a housing 318 enclosing electronic components. The display screen and/or the protective shield 310 may include a coating that provides variable contrast to enhance viewability of displayed information while subject to a range of ambient brightness. The protective shield 310 may provide a variable focal point (diopter). The protective shield 310 can be flipped from a stored up-position to a protective down-position (as shown in FIG. 3) to cover an outside surface of the display screen that faces a patient and function to protect the display screen from fluids and other materials occurring during a procedure. The display screen can be moved by a user through a two-arm friction-joint linkage 312 that provides telescopic and up-and-down adjustment of location of the housing 318 to enable a user to position the display screen at a location providing convenient visual reference. A ball-and-socket joint 316 is connected between the linkage 312 and the housing 118 to provide planar adjustment for the display screen. The linkage 312 is connected to the headband 120 through a pivot joint 314 to allow the user to flip the housing 318 and connected display screen up and down. The display screen can thereby be flipped-up outside the user's line-of-sight or the user's peripheral vision when not being used.

Figure 4:
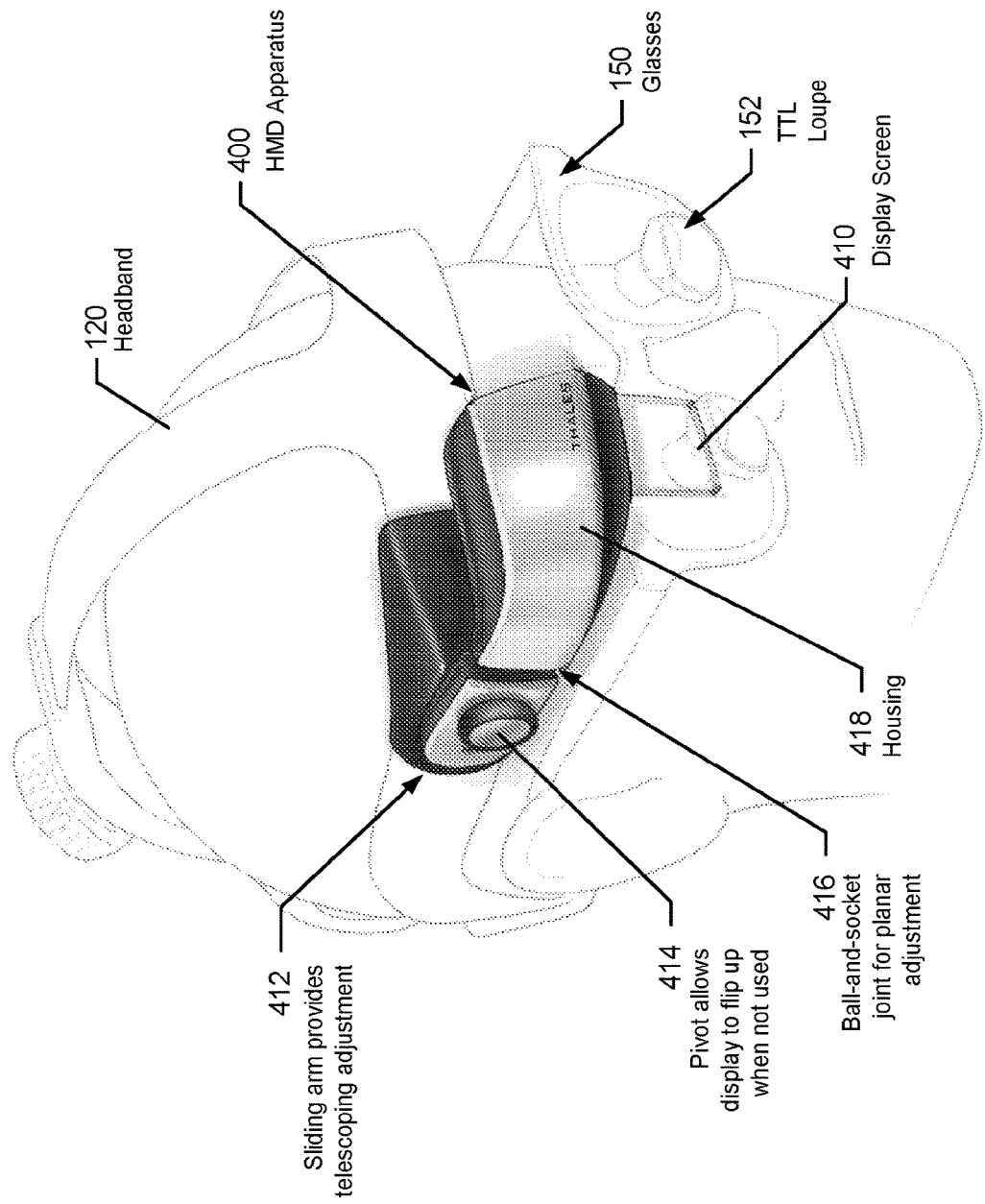

FIG. 4 illustrates another HMD 400 configured according to some embodiments of the present disclosure. The HMD 400 includes a display screen 410 that extends downward from a housing 418 enclosing electronic components. The display screen 411) and housing 418 are connected to a ball-and-socket joint 416 which provides planar adjustment for the display screen 410. The ball-and-socket joint 416 is connected to a pivot 414 that allows the housing 418 and connected display screen 410 to be pivoted up and down, so that the display screen 410 can be flipped-up outside the uses line-of-sight or the uses peripheral vision when not being used. The pivot 414 is connected to a sliding arm 412 that connects to the headband 120. The sliding arm 412 provides telescoping adjustment to allow user placement of the display screen 410 a desired distance from an eye.

Figure 5:
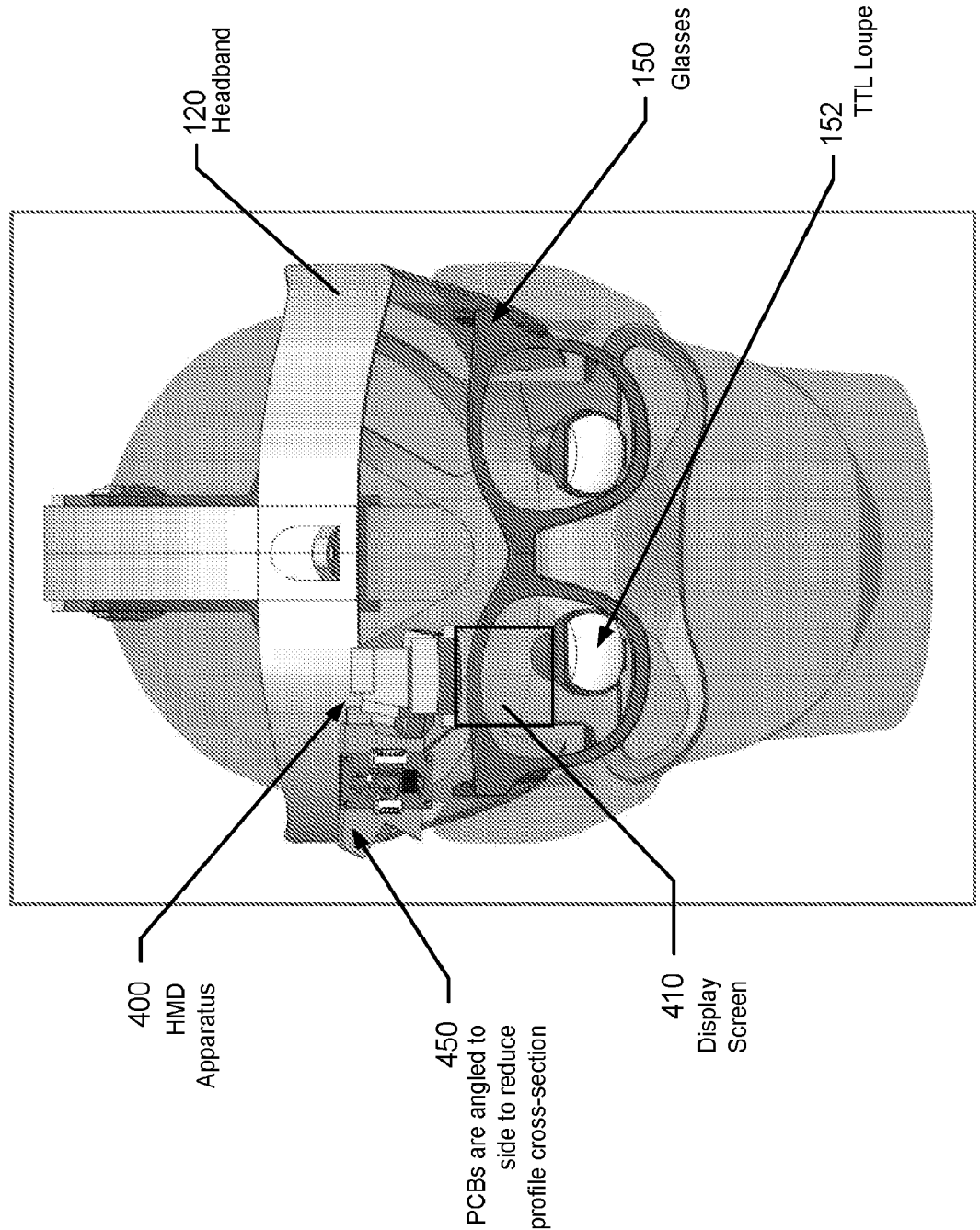

FIG. 5 illustrates a front view of the HMD 400 of FIG. 4 with the housing 418 removed to expose printed circuit boards (PCBs) 450 which operationally connect the electronic components mounted thereon. The electronic components display images on the display screen 410, and may operate in combination with integrated or remote computer equipment to sense and interpret movement of the head, sense and interpret gestures made by a user's hands, eyes, or other objects, and/or sense and interpret voice commands by the user. The PCBs 450 are tilted at a defined non-zero angle relative to vertical to reduce the profile cross-section of the housing 418. For example, the PCBs 450 can extend generally diagonally across the housing 418.

Figure 7:
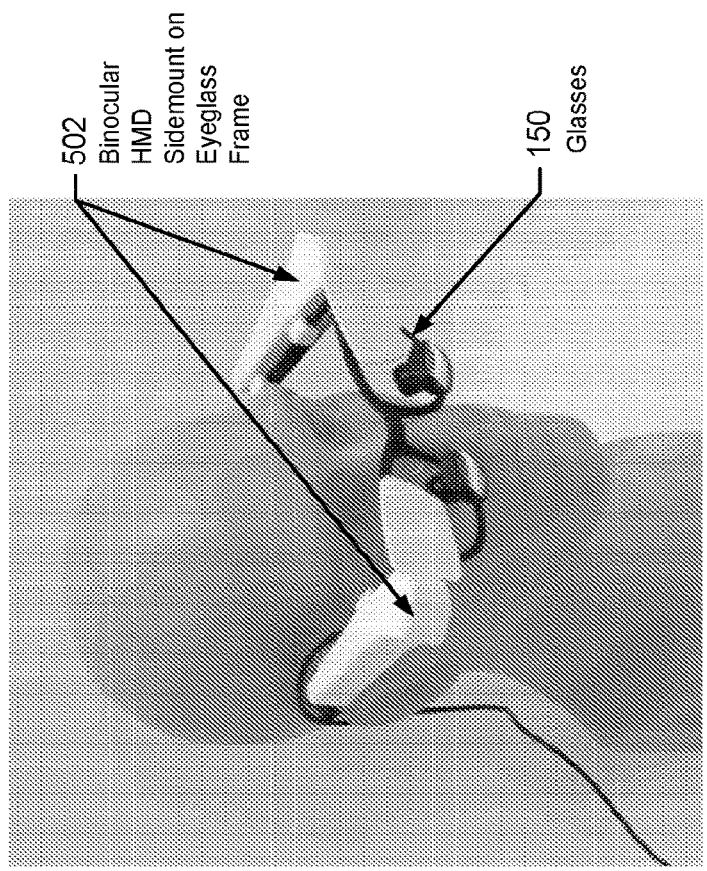
Figure 6:
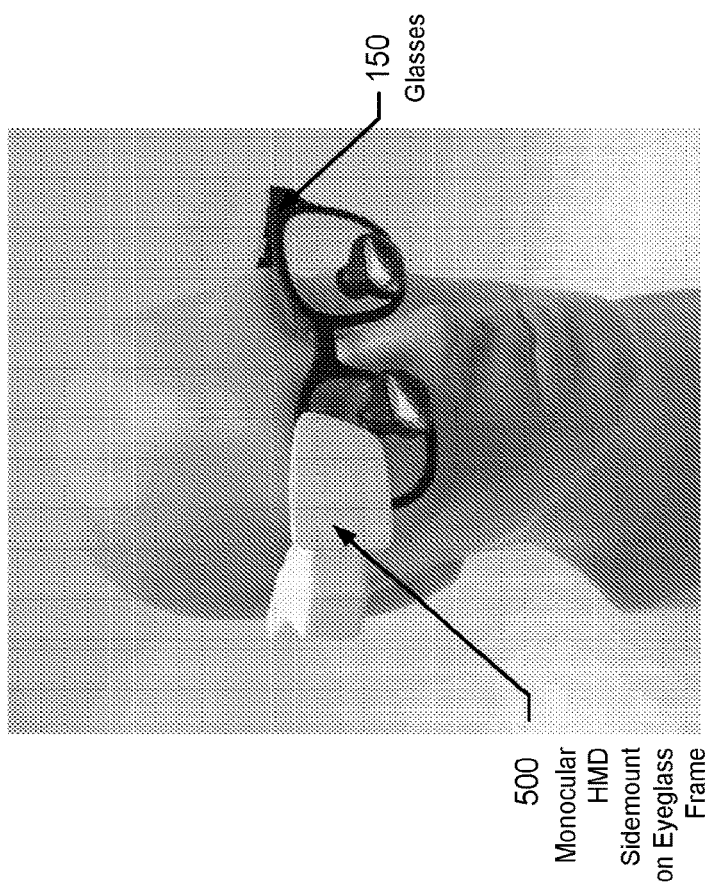

FIG. 6 illustrates another HMD 500 having a single display screen connectable to an eyeglass frame to provide monocular viewing by the user. FIG. 7 illustrates another HMD 502 including a pair of display screens that are connectable to opposite sides of an eyeglass frame to provide binocular viewing. Although the display screens in FIGS. 6 and 7 are shown as being opaque, they may instead allow a user to see through the display screen while viewing information displayed thereon.

Figure 8:
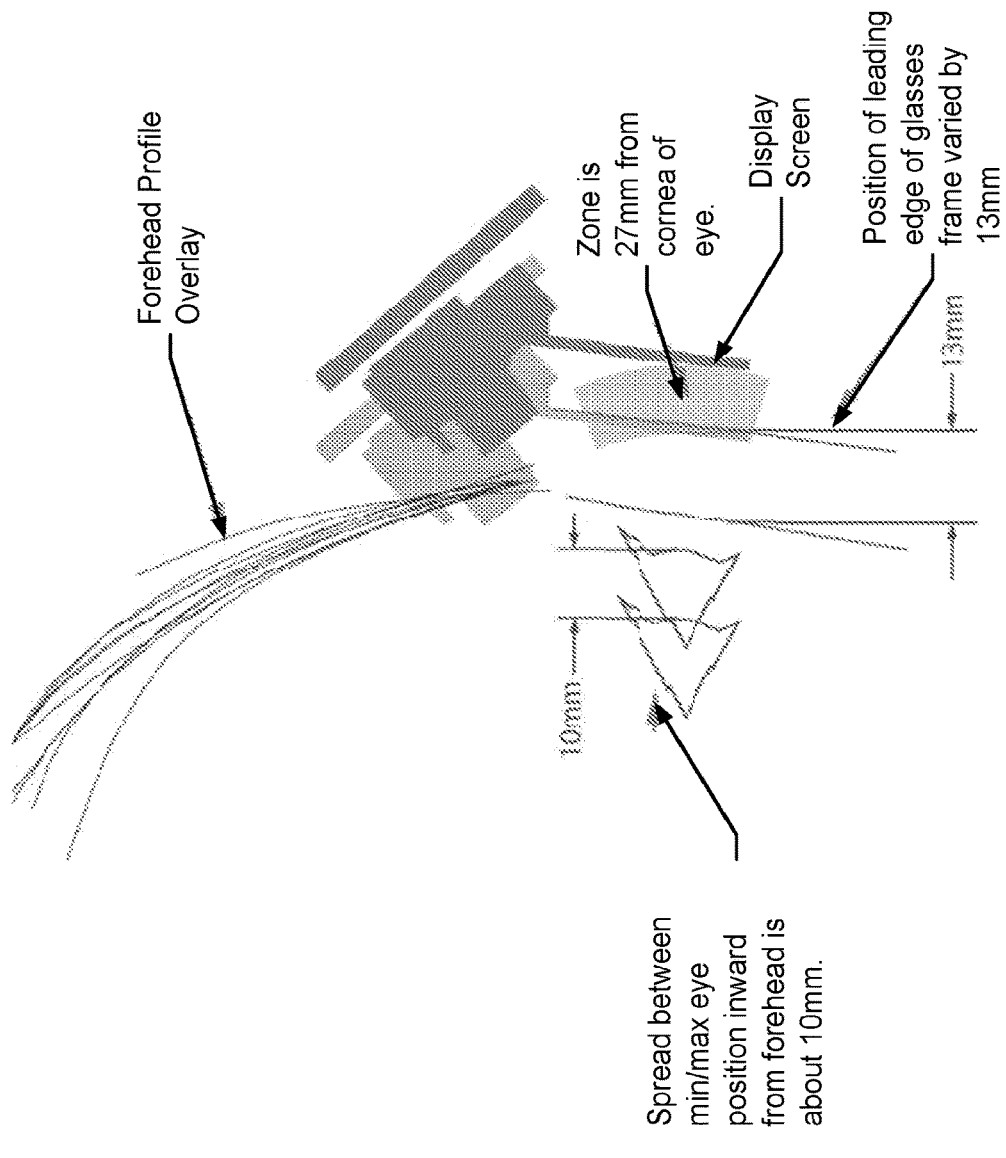

FIG. 8 illustrates example design parameters that may be used when configuring a HMD to allow movement of the display screen to accommodate anticipated variation in user head geometries. Referring to FIG. 8, the spread between the minimum and maximum eye position inward from the forehead is about 10 mm. Consequently, the HMD may preferably be configured to allow variation in the distance between the display screen and a user's eye of up to 27 mm and, more preferably, 13 mm.

Example Computer System Incorporating a Head Mounted Display Apparatus

Figure 9:
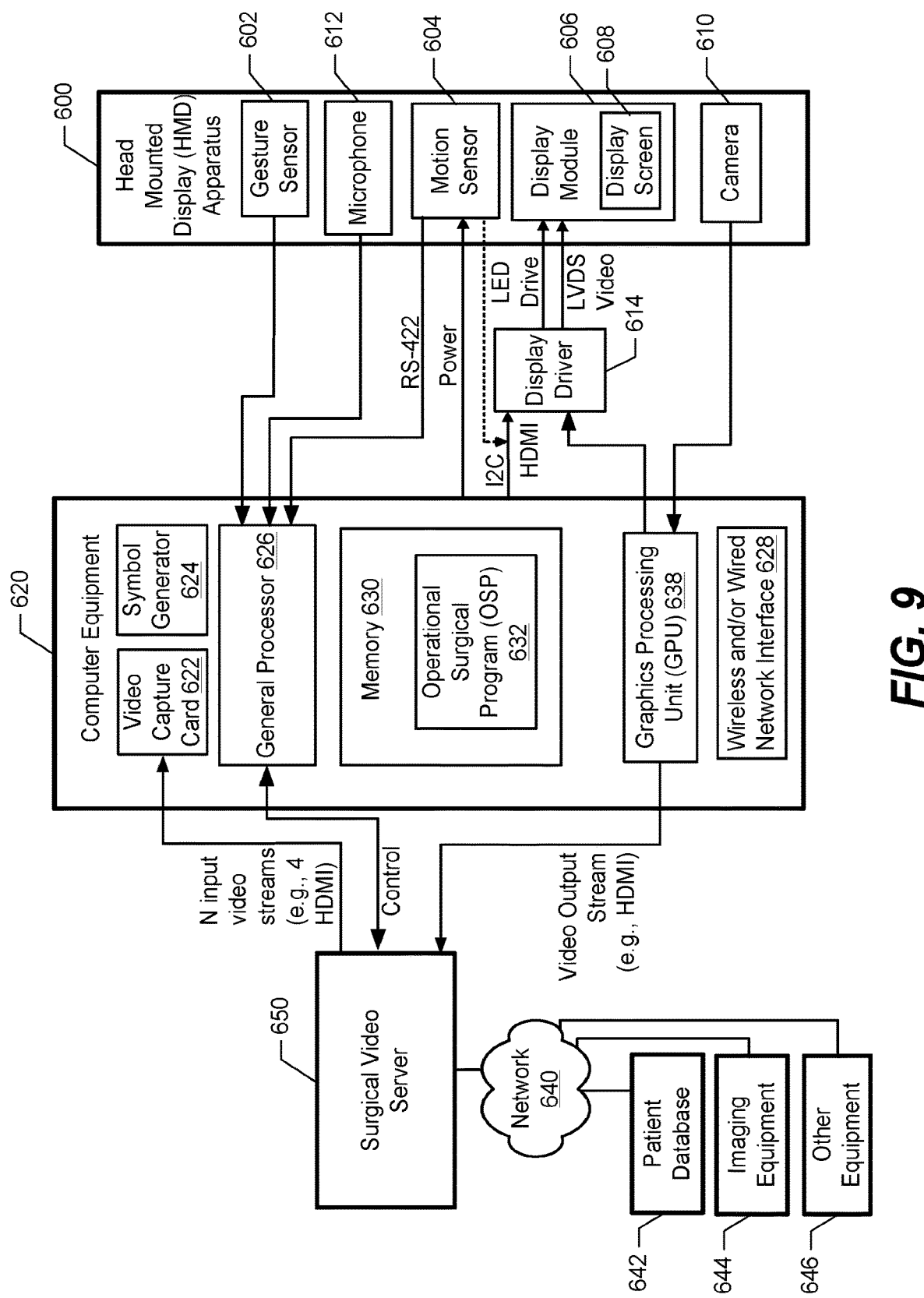
FIG. 9 is a block diagram of electronic components of a computer system that includes a head mounted display apparatus configured according to some embodiments of the present disclosure.

FIG. 9 is a block diagram of electronic components of a computer system that includes a HMD apparatus 600, computer equipment 620, and a surgical video server 650. The video server 650 can be connected via a data network 640 to a patient database 642, imaging equipment 644, and other electronic equipment 646. The HMD 600 may correspond to any of the HMDs of FIGS. 1-8. Although the computer equipment 620 is illustrated as being separate from the HMD 600, some or all of the operations disclosed herein as being performed by the computer equipment 620 may additionally or alternatively be performed by one or more processors residing within the HMD 600. Similarly, some of the operations disclosed herein as being performed by the HMD 600 may additionally or alternatively be performed by one or more processors residing within the computer equipment 620.

The video server 650 can receive, store, and route information, video streams between the patient database 642, imaging equipment 644, and other electronic equipment 646 and the HMD 600. As used herein, a video stream can include any type of information that can be provided to a display device for display, including without limitation a still image (e.g., digital photo), a sequence of still images, and video having frames provided at a defined frame rate. The imaging equipment 644 may include endoscope cameras, magnetic resonance imaging equipment, computed tomography scanning equipment, three-dimensional ultrasound equipment, endoscopic equipment, and/or computer modeling equipment which can generate multidimensional (e.g., 3D) model based on combining images from imaging equipment 644. The patient database 642 can retrievably store information relating to a patient's medical history, and may store patient images from earlier procedures conducted via the imaging equipment 644. The other equipment 646 may provide information relating to real-time monitoring of a patient, including, for example, hemodynamic, respiratory, and electrophysiological signals.

The computer equipment 620 operationally interfaces the HMD 600 to the video server 650. The computer equipment 620 includes a video capture card 622 that can simultaneously receive a plurality (N) of video streams and information (e.g., textual descriptions, audio signals, etc.) from the video server 650 and/or directly from the imaging equipment 644, the patient database 642, and/or the other equipment 646. The computer equipment 620 may communicate with the video server 650, the HMD 600, and other equipment of the system via a wireless and/or wired network interface 628 using any appropriate communication medium, including but not limited to a wireless air interface (e.g., 3GPP Long Term Evolution (LTE), WLAN (EEE 802.11), WiMax, etc.), wireline, optical fiber cable, or any combination thereof. In the example embodiment of FIG. 9 the video capture card 622 simultaneously receives up to 4 video streams via 4 HDMI interfaces. In one embodiment the HMD 600 is communicatively connected to the computer equipment 620 via an HDMI cable, a USB or RS 422 cable connected to the motion sensor 604 and/or gesture sensor 602, and a USB 3.0 or firewire cable connected to the camera 610. A microphone 612 can be connected to the computer equipment 620. The video and/or sensor signaling may alternatively be communicated between the HMD 600 and the computer equipment 620 through a wireless air interface, such as the network interface 628.

The HMD 600 includes a display module 606 that processes and displays video and other images on the display screen 608 (e.g., a LCD display, a reflective screen on which the display module 606 projects images, etc.) for viewing by a user. It may be preferable for the display screen 608 to be a see-through display device allowing the user to see displayed video superimposed on what is viewed through the display screen 608. The video streams received by the video capture card 622 are processed by a graphics processing unit (GPU) 638, conditioned by a display driver 614, and provided to the display module 606 for display on the display screen 608. A symbol generator 624 may add graphical indicia and/or textual information to the video stream(s) provided to the HMD 600 based on information received from the video server 650 (e.g., via the patient database 642).

The display driver 614 may reside in the computer equipment 620 or the HMD 600. In one embodiment, the display driver 614 receives video via a HDMI interface from the GPU 638, and converts the digital video signal to an analog video signal which is output as low-voltage differential signaling (LVDS) to the display module 606. The display driver 614 may also provide power and/or other signaling to the display module 606 via a LED drive signal.

The HMD 600 can include a camera 610, or a plurality of the cameras 610, facing away from the user that outputs video and/or other images via the wireless and/or wired network interface 628, illustrated as a HDMI cable in FIG. 9, to the GPU 638 for processing and relay to the video server 650 for storage and possible further relay to other HMDs 600 worn by other personnel assisting with the procedure. For example, the camera 610 may be configured to be aligned with the user's line-of-sight when the user has adjusted the display screen 608 to be comfortably viewed by the user. A video signal from the camera 610 can be processed through the computer equipment 620 and provided to the video server 650 for recording what the user is viewing during the procedure and/or can be provided as a real-time video stream to other HMDs 600 worn by personnel assisting with the procedure so that the personnel can observe what the user is seeing. The video signal from the camera 610 may be augmented by the symbol generator 624 with one or more designation symbols. The augmented symbols may, for example, identify the user as the source of the video stream and/or be added to a video stream by the user to identify observed features, such as a patient's anatomy.

The HMD 600 may include a motion sensor 604 and/or a gesture sensor 602. The motion sensor 604 may be a gyroscope, accelerometer (e.g., a multi-axis accelerometer), and/or tilt sensor that outputs a head motion signal indicating a measurement of movement of the user's head while wearing the HMD 600. The motion sensor 604 may be powered by the computer equipment 620 and may output the head motion signal via, a communication interface, such as a RS-422 serial digital interface. For example, the motion sensor 604 may output a head motion signal that indicates yaw movement (i.e., rotation of the user's head left or right) and/or indicates pitch movement (i.e., rotation of the user's head up or down).

The motion sensor 604 may be a sourceless orientation sensor. The head motion signal may be processed by the HMD 600 and/or by the computer equipment 620 to compensate for drift error introduced by the motion sensor 604. In one embodiment, one directional reference (e.g., yaw) component of the head motion signal is corrected toward zero responsive to another reference component (e.g., pitch) of the head motion signal being within a threshold offset of a defined value. For example, yaw drift error in the head motion signal can be determined based on monitoring yaw values of the motion signal while the user is looking down at a defined pitch (e.g., pitch being within a threshold range of a defined value) to align the user's eyes with an object (e.g., when a surgeon repetitively looks down to view a surgical site of a patient). In one embodiment, responsive to the pitch component of the head motion signal indicating that a surgeon is looking down for at least a threshold time that is indicative of the surgeon visually concentrating on a surgical site, the computer equipment 620 assumes that the HMD 600 is stabilized along the yaw axis and computes yaw drift error based on measured change in the yaw component over a defined time interval. The head motion signal is then compensated to remove the determined yaw drift error. In another embodiment, the computer equipment 620 measures drill in the yaw component of the head motion signal while a static image is displayed on the display screen, assuming that the surgeon's head is stabilized along the yaw axis, and then compensates the head motion signal to remove the measured drift in the yaw component.

The head motion signal may be processed by the HMD 600 and/or by the computer equipment 620 to identify an origin for one or more directional reference components from which movement is referenced. For example, an origin location from which yaw is measured may be identified based on an average (e.g., median or mode) of a yaw component of the head motion signal during times when the user is looking down at a defined pitch to align the user's eyes with an object (e.g., surgeon looking down to view a surgical site).

The directional reference (e.g., pitch or yaw) of the head motion signal, which is defined to trigger compensation for drift error and/or which is defined as a reference origin for movement measurement, may be identified based on the user maintaining a substantially constant orientation of the HMD 600 for a threshold time (e.g., dwell time). For example, when a surgeon has maintained a relatively constant head position while viewing a surgical site of a patient for a threshold time, the directional reference (e.g., pitch or yaw) of the head motion signal during that dwell time can be used as a basis for compensating for drift error and/or setting as a reference origin for display of virtual display panels illustrated in FIGS. 10-12. In one embodiment, the head motion signal may be processed by the HMD 600 and/or by the computer equipment 620 to estimate gyroscope bias(es) giving rise to yaw drift and/or pitch drift accumulating over time based on pseudo-measurements of the yaw and/or the pitch provided by the head motion signal which is expected to be nearly zero each time the surgeon looks down at the same surgical site and steadies the head to center the line-of-sight at a same location on the patient.

The gesture sensor 602 may include any type of sensor that can sense a gesture made by a user. In a surgical environment, use of a gesture sensor 602 to receive a gesture-based command from a surgeon or other OR personnel can be advantageous because it avoids a need for the user to touch a non-sterile surface of the HMD 600 or other device. The gesture sensor 602 may include the camera 610 which outputs video (e.g., RGB-D video) displaying movement of a user's hand, fingers, arms or other objects moved by the user along a pathway that the user knows will define a command identifiable by an operational surgical program (OSP) 632 and/or another component of the system. The camera 610 or another camera may be directed toward one of the user's eyes to identify a dwell time of the eye, blink timing, and/or movement of the eye to generate a command from the user to control what is displayed on the display screen 608.

The gesture sensor 602 may alternatively or additionally include one or more photoelectric motion and/or proximity sensors. In one embodiment, the gesture sensor 602 has a plurality of infrared emitters and a plurality of photodiodes. Adjacent pairs of an infrared emitter and a photodiode are spaced apart and arranged to form a directional array facing outward from a housing of the HMD 600 to sense presence of a user's hand adjacent to the array and/or to sense a direction of movement as the user's hand is moved across the array. A user may, for example, swipe a hand in a first direction across the array ((without touching the housing) to input a first type of gesture recognized by the OSP 632 processed by the processor 626 which triggers a first type of operation by the OSP 632, swipe the hand in a second direction about opposite to the first direction across the array to input a second type of gesture recognized by the OSP 632 which triggers a second type of operation by the OSP 632, swipe the hand in a third direction about perpendicular to the first direction across the array to input a third type of gesture recognized by the OSP 632 which triggers a third type of operation by the OSP 632, and so on with other directions of movement being identifiable as other types of gestures provided by the user to trigger other types of operations by the OSP 632.

In another embodiment the gesture sensor 602 includes an ultrasonic echo ranging transducer that senses signal echo reflections from a user's hand and outputs a signal to the processor 626 which identifies gestures formed by movement of the hand. In another embodiment the gesture sensor 602 includes a capacitive sensor that senses presence of a user's hand through capacitive coupling between a charge plate and the user's hand. A plurality of capacitive sensors may be spaced apart to form the gesture sensor 602 and configured to sense a direction of movement of the user's hand relative to the array of charge plates (e.g., sense an order with which plates experienced increased coupling to the user's hand). Different sensed directions of movement can be interpreted by the OSP 632 and/or another component of the system as representing different commands selected by the user for operation.

The HMD 600 can include a microphone 612 configured to receive voice commands from a user. The processor 626 executing the OSP 632 and/or another component of the system can be configured to recognize a received voice command as corresponding to one of a plurality of defined voice commands, and trigger operation of a command corresponding to the recognized voice command to control information displayed on the display screen 608.

The computer equipment 620 includes a general processor 626 and memory 630. The processor 626 may include one or more data processing circuits, such as a general purpose processor and/or special purpose processor, such as a microprocessor and/or digital signal processor. The processor 626 is configured to execute computer program code in the memory 630, described below as a non-transitory computer readable medium, to perform at least some of the operations described herein. The computer program code may include the OSP 632. The OSP 632 when executed by the processor 626 causes the processor 626 to perform operations in accordance with one or more embodiments disclosed herein. The computer equipment 620 may further include a speaker, a user input interface (e.g., touch screen, keyboard, keypad, etc.), a display device, etc.

In one embodiment, the video signal from the camera 610 is displayed on the display device 608 of the same HMD 600, and the symbol generator 624 in combination with the OSP 632 processed by the processor 626 may operate to display graphical indicia (e.g., reticle) that can be positioned within a plane of the video stream by the user responsive to recognition of voice commands via the microphone 612, to track movement of the user's finger, hand, or other object recognized in the video stream responsive to the gesture sensor 602 (e.g., via the camera 610), and/or to track motion sensed by the motion sensor 604. The user may trigger the OSP 632 to capture a still image from the video stream with the incorporated graphical indicia responsive to a voice command, a gesture sensed by the gesture sensor 602, and/or a motion sensed by the motion sensor 604. In this manner, a surgeon may view video of a surgical site and steer a graphical indicia to be aligned within the video overlapping a point-of-interest in the patient's anatomy, and trigger capture of a still image including the video and graphical indicia that can be saved on the video server 650 and/or distributed to another HMD 600 for viewing by another surgeon or person.

In a further embodiment a user can view video from the camera 610 and steer a graphical indicia to be aligned with a location within a plane of the video stream, and can trigger recordation of the present positional alignment of the camera 610. The OSP 632 may then operate to maintain alignment of the graphical indicia displayed in the display screen 608 between, for example, the user's visual line-of-sight and the defined location as the user moves the HMD 600 (i.e., rotates the head up/down and/or right/left).

As the user looks away from the defined location, the OSP 632 responds to the head motion signal by correspondingly moving the graphical indicia across the display screen 608 maintaining visual alignment with the defined location until it is no longer displayed when the defined location is no longer in the user's field of view, and similarly as the user looks back toward the defined location the OSP 632 responds to the head motion signal by making the graphical indicia reappear on a corresponding edge of the display screen 608 and then further track movement to maintain visual alignment with the defined location as the user continues to rotate the HMD 600 toward the defined location. In this manner, a surgeon can virtually mark a location within a surgical site using a graphical indicia and can subsequently track that marked location based on the location of the graphical indicia within the display screen 606 while the surgeon's head moves. The graphical indicia may be included in a video stream from the camera 610 that is communicated, e.g., as a real-time video stream, to another HMD 600 worn by another person and/or that is communicated to the video server 630 for recordation and/or forwarding to other devices.

The computer equipment 620 may compare patterns of objects in the video stream from the camera 610 viewing a patient's anatomy to patterns of objects in other video (e.g., images, etc.) from the video server 630 and/or the imaging equipment 644 to identify levels of correspondence (e.g., output by a pattern matching algorithm). The computer equipment 620 may display indicia in the display screen 608 responsive to identifying a threshold level of correspondence between compared objects. For example, real-time video captured by the camera 610 during surgery of a patient may be processed by the computer equipment 620 and compared to video captured by one or more other sources. The other source(s) can include real-time feeds and/or earlier stored video provided by, for example, ultrasound equipment, cameras, CT scans, etc. The other source(s) may additionally or alternatively include an anatomical database specific for the particular patient or more generally for humans. The pattern matching may be constrained to characteristics of an object or a set of objects defined by a surgeon as being relevant to a present procedure. The computer equipment 620 may display on the display screen 608 an indicia (e.g., a crosshair or color marker) aligned with the identified object within the video from the camera 610 to assist the surgeon with identifying a location within the object of interest. The video sources may include an embedded marker that indicates a location within an object that is of interest to the surgeon. The pattern matching may further identify a location within the video stream from the camera 610 that corresponds to a location of the marker in the compared video, and an indicia may be displayed on the display screen 608 aligned with the location within the video from the camera 610 to assist the surgeon with identifying the location within the object of interest.

In some other embodiments, the user operates a handheld (e.g., wireless controller) control panel and/or a foot control panel to provide commands or other input to control operation of the computer equipment 620. A handheld control panel and/or foot control panel may be operated to select among a plurality of video streams that are provided to the HMD 600 for viewing, control magnification of the video stream provided to the HMD 600, control the location of a graphical indicia displayed within a video stream, control stop-start recordation of a video stream from the camera 610, and/or control routing of video streams and other information between the HMD 600, the video server 650, other HMDs 600, and other components of the system.

For example, a user may operate a portable computer, such as a laptop computer, tablet computer, mobile phone, or wearable computer to control the display of information on the display screen 608. For example, a tablet computer may be configured to select among a plurality of virtual display panels for display on the display screen 608. The tablet computer may select among the virtual display panels responsive to a user moving (e.g., rotating) the tablet computer, responsive to identifying a hand gesture via a camera of the tablet computer and/or via a touch sensitive display of the table computer, and/or responsive to recognizing a voice command via a microphone of the tablet computer. A user may, for example, rotate the tablet computer horizontally to scroll through a plurality of virtual display panels that are virtually organized along a horizontal plane. The user may similarly rotate the table computer vertically to scroll through a plurality of virtual display panels that are virtually organized along a vertical plane.

Virtual Displays Controlled by Head Mounted Display Apparatus

The computer equipment 620, via operation of the OSP 632, can generate virtual display panels that display video received from the video server 650 and/or other components of the system, and control which of the virtual display panels are presently displayed on the display screen 608 for viewing by a user based on user commands identified from motion sensed by the motion sensor 604, a gesture made by the user which is sensed by the gesture sensor 602 and/or the camera 610, and/or a voice command via the microphone 612. The virtual display panels can be arranged and visually presented to the user to visually appear to float within space in front of the user. The user's head may be rotated up and down and/or right and left to observe content of different ones of the virtual display panels that appear to retain a static position in space relative to the user's head. The user may alternatively or additionally make a gesture, such as by moving a hand left or right and/or moving the hand up or down, to cause the virtual display panels to correspondingly slide left or right and/or up or down.

The display screen 608 may be controlled to display only one of the virtual display panels at a time, such as by switching from one virtual display panel to another adjacent virtual display panel, or display a more continuous panning across the virtual display panels through which a user may view portions of two or more adjacent virtual display panels.

In case the user finds it undesirable to read the virtual display panels moving under control of the computer equipment 620 while looking around, the computer equipment 620 may enable the user to input a command (e.g., "Lock") which causes whichever virtual display panel is presently most closely spaced to the user's line-of-sight to be displayed full screen and held statically in-place not responding to head movement. The virtual display panel may remain statically locked as-displayed until the user deactivates the command via, for example, another command (e.g., "Unlock").

The computer equipment 620 may be configured to provide an automatic-lock and/or unlock of a virtual display panel relative to the display screen 608. When an automatic mode is enabled, a virtual display panel becomes automatically locked relative to the display screen 608 when the user's line-of-sight (e.g., yaw and pitch) indicated by the head motion signal is within a first threshold amount (e.g., 2°) offset from a defined location (e.g., yaw and pitch) of the virtual display panel. The computer equipment 620 may be configured to automatically unlock the virtual display panel from the display screen 608 when the user's line-of-sight (e.g., yaw and pitch) indicated by the head motion signal becomes at least a second threshold amount (e.g., 5°), which is greater than the first threshold amount, offset from the defined location (e.g., yaw and pitch) of the virtual display panel. The threshold amounts may be defined and/or adjusted by the user, and may be stored as a user's preference in the user's account information for subsequent retrieval and use.

Figure 10:
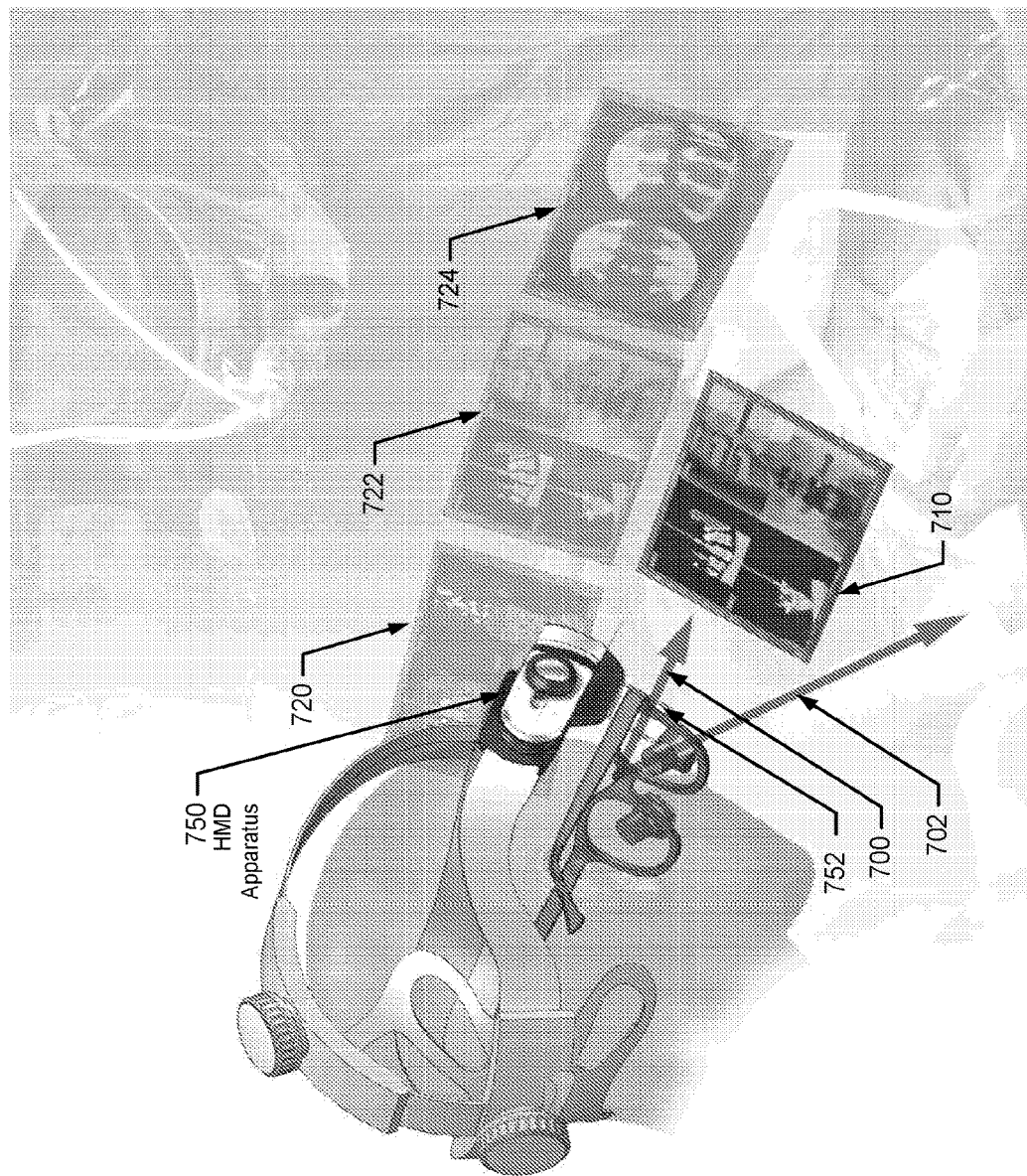
FIGS. 10-12 illustrate operations and methods that may be performed by a system that includes a head mounted display apparatus to control the display of virtual display panels through a display screen of a head mounted display apparatus according to some embodiments of the present disclosure.
Figure 11:
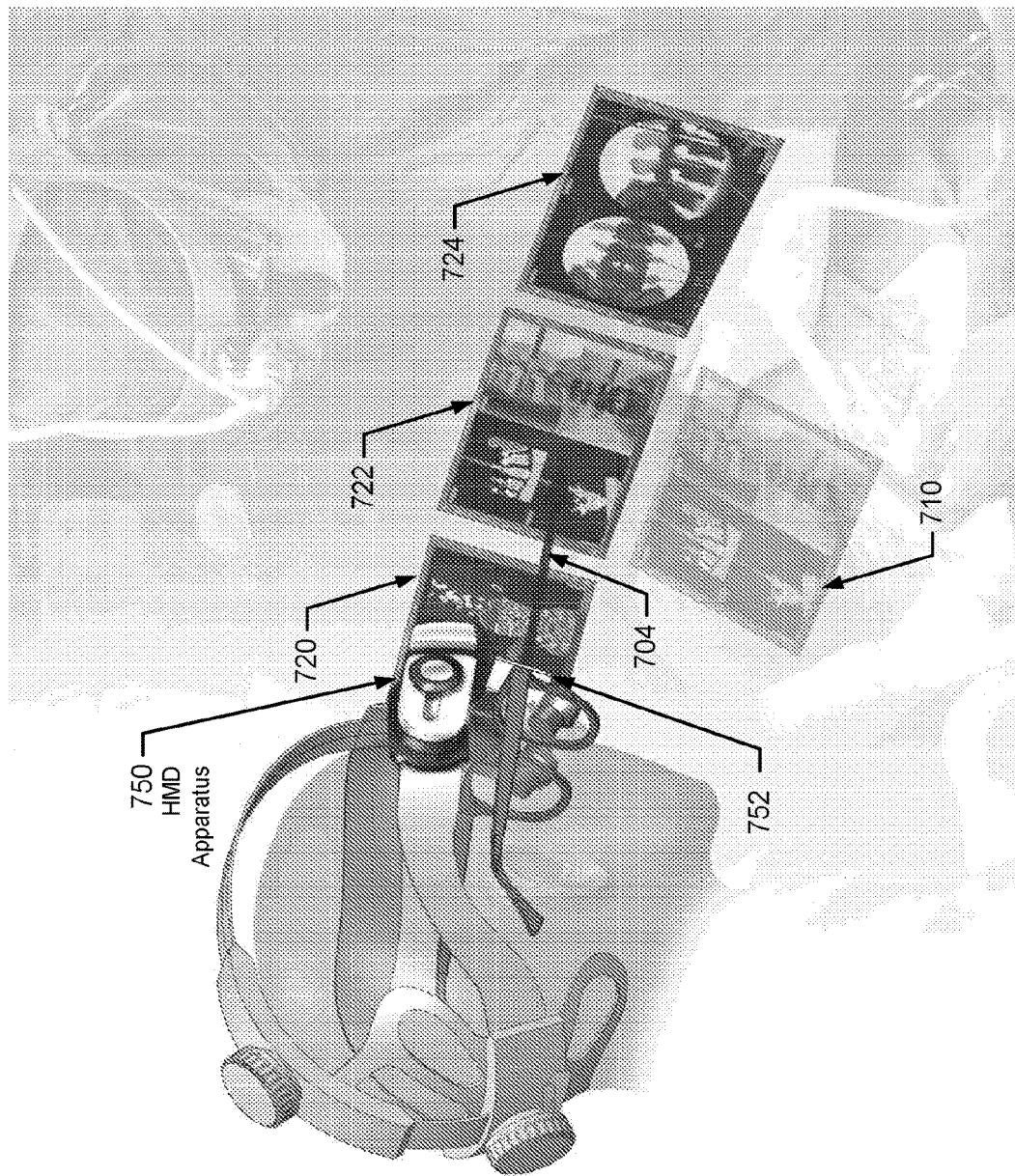
Figure 12:
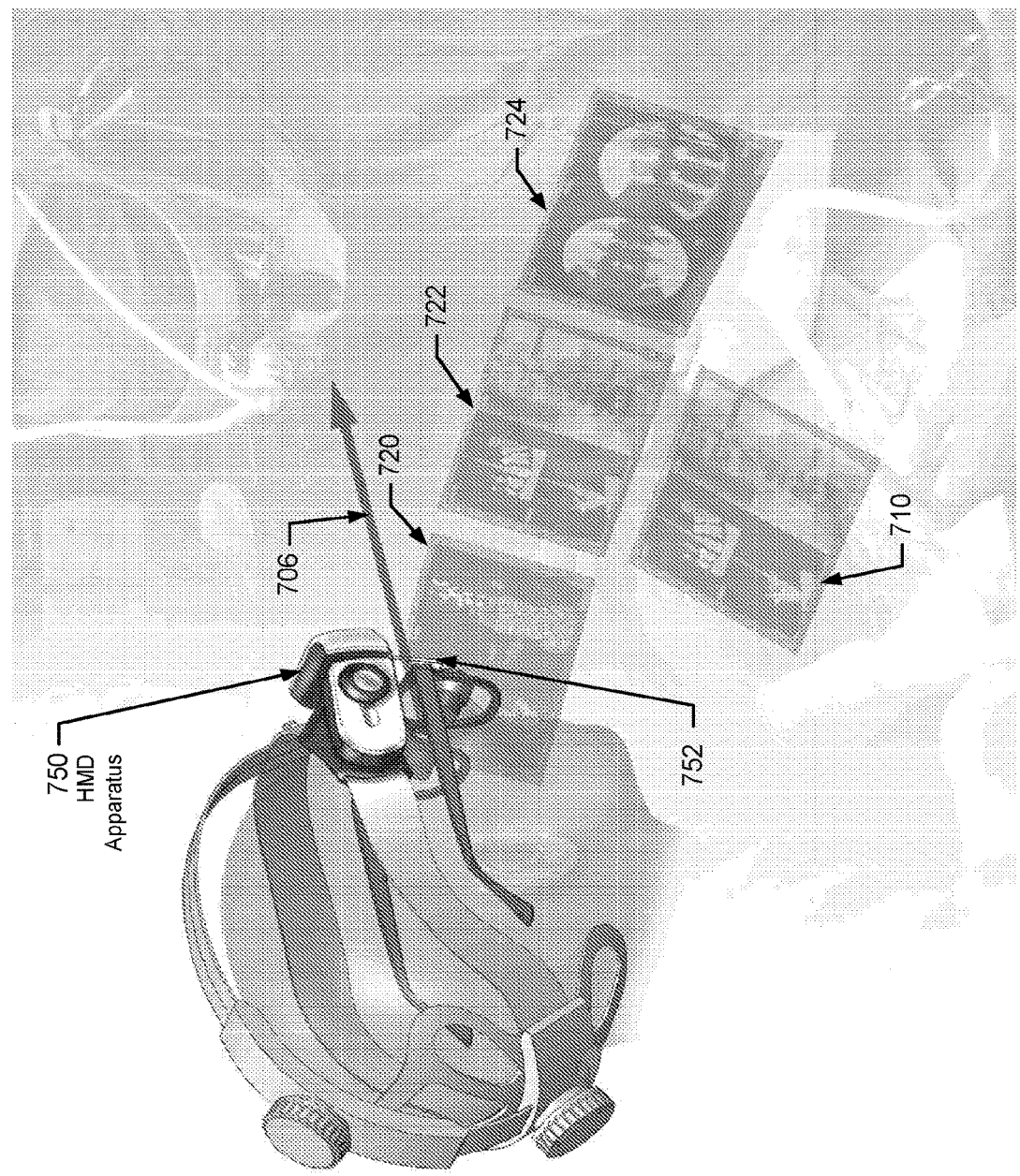

FIGS. 10-12 illustrate operations and methods that may be performed by a system including a HMD 750 to control the display of virtual display panels through a display screen 752 of the HMD 750 according to some embodiments of the present disclosure. The various operations and methods described in the context of FIGS. 10-12 are not limited to use with the particular configuration of virtual display panels that are illustrated, but instead may be used with any number of virtual display panels and any arrangement of virtual display panels. Some of the virtual display panels may be displayed immediately adjacent to one another to appear as a single larger virtual display panel. Moreover, although various embodiments are described in the context of a particular HMD 750 configuration used in a surgical environment, the operations and methods may be used with any HMD 750 configuration for any type of operational use.

The example embodiments of FIGS. 10-12 allow a surgeon or other user to see several virtual displays of different medical information without looking away from the surgical site and focusing far away to view physical monitors that may be mounted across the OR or elsewhere adjacent to the patient. In some embodiments, three operational "modes" of the virtual displays are selectively activated based upon pitch of the surgeon's head and the corresponding viewing line-of-sight of the user. The three operations may be separately activated by increasing pitch angle of the HMD 750 through three corresponding ranges of viewing angles, such as low (directly at the surgical space), medium, high (horizontal eye-level). The viewing angle of the surgeon can be determined from the head motion signal output by a motion sensor of the HMD 750.

A full-screen operational mode is triggered when the OSP 632 determines that the surgeon is looking down at an operation site, which may be determined by when the pitch is below a first pitch threshold (e.g., about −45°). The first pitch threshold may be defined and/or adjusted by the surgeon based on a voice command, entered through a physical user interface, etc. In the full-screen operational mode, a defined one of the video streams (e.g., a primary video stream received via HDMI channel A) is displayed full screen through a display screen 752 of the HMD 750. The surgeon's corresponding preference settings may be saved in a configuration file stored in the memory 630 with an identifier for the surgeon, so that the surgeon's preferred settings can be automatically retrieved upon recognition of the surgeon (e.g., via a login process through the computer equipment 620).

Referring to FIG. 10, the computer equipment 620, as illustrated in FIG. 9, receives four video streams which it separately maps, via the OSP 632, to four different virtual display panels 710, 720, 722, and 724. Alternatively, the computer equipment 620 may combine two or more video streams to generate a combined video stream that is mapped to one of the virtual display panels 710, 720, 722, and 724. The computer equipment 620 may add graphical indicia and/or other information to one or more of the video streams, such as explained above. The computer equipment 620 can arrange the virtual display panels in two-dimensional space or in three-dimensional space. In the example of FIG. 10, three of the virtual display panels 720, 722, and 724 are arranged horizontally along an upper row designated as secondary virtual display panels, and the fourth virtual display panel 710 is arranged below the center virtual display panel 722 and designated as a primary virtual display panel. Other arrangements of the virtual display panels 710, 720, 722, and 724 may be provided, and other numbers of virtual display panels may be generated by the computer equipment 620 with corresponding mapping to any number of video streams.

In the example of FIG. 10, the surgeon's head is tilted downward below the first pitch threshold so that the surgeon's line-of-sight 702 is toward the operation site while looking through the TTL loupe. The surgeon may shift eye position upward so that the surgeon's line-of-sight 700 now looks through the display screen 752. The computer equipment 620 responds to the surgeon's head tilted below the first pitch threshold by operating in the full-screen operational mode to select a defined one of the video streams which it displays on the display screen 752 to generate the primary virtual display panel 710. Accordingly, the primary virtual display panel 710 can be positioned by the HMD 750 to appear to the surgeon, while maintaining the line-of-sight 700, to hover in space above and adjacent to the location of the operation site. None of the three other video streams mapped to the three secondary virtual display panels 720, 722, and 724 are presently displayed on the display screen 752.

FIG. 11 illustrates operations triggered by when the surgeon's head tilts up above the first pitch threshold and below a second pitch threshold so the surgeon's line-of-sight is along line 704 through the display screen 752. The primary virtual display panel 710 disappears from the display screen 752 and the three video streams (e.g., HDMI channels B, C and D) become separately viewable or at least partially collectively viewable as the three secondary virtual display panels 720, 722, and 724 floating in space. These secondary virtual display panels 720, 722, and 724 may first appear at default radial positions on a sphere centered in the surgeon's head, but the surgeon can have the ability to reposition and resize them for maximum convenience.

The collection of virtual display panels may be displayed as virtual floating monitor devices that are stationary in location, so that the user can move the HMD 750 to scan across their spaced apart locations and see individual ones of the virtual display panels. The surgeon can scroll sideways across the secondary virtual display panels 720, 722, and 724 by making corresponding sideways (e.g., yaw) head movements, by making defined gestures, and/or by speaking defined voice commands. The surgeon can similarly scroll downward from the secondary virtual display panels 720, 722, and 724 to view the primary virtual display panel 710 by making a corresponding downward (e.g., pitch) head movement, by making a defined gesture, and/or by speaking a defined voice command.

The computer equipment 620 may enlarge or shrink a portion of a video stream displayed on one of the virtual display panels being viewed by a surgeon responsive to a defined gesture by the surgeon and/or a defined voice command by the surgeon.

The symbol generator 624 in combination with the OSP 632 processed by the processor 626 of the computer equipment 620 may operate to display a graphical indicia (e.g., crosshair or other reticle) that can be positioned within a presently viewed one of the virtual display panels by the user responsive to recognition of voice commands via the microphone 612, to track movement of the user's finger, hand, or other object operationally recognized by the gesture sensor 602 and/or in a video stream from the camera 610. The user may trigger the OSP 632 to capture a still image of the video stream displayed in the virtual display plane with the incorporated graphical indicia responsive to a voice command, a gesture sensed by the gesture sensor 602, and/or a motion sensed by the motion sensor 604. In this manner, a surgeon may view video within one of the virtual display panels and steer a graphical indicia to be aligned within the video overlapping a point-of-interest, and trigger capture of a still image including the video and graphical indicia that can be saved on the video server 650 and/or distributed to another HMD 600 for viewing by another surgeon or assistant.

For example, the user may trigger display a crosshair indicia responsive to a voice command (e.g., "Crosshair On"). The graphical indicia may initially appear at the center of the display screen 608. Then, when the user has repositioned the crosshair indicia on an item to be marked, the user can speak another command (e.g., "Freeze") to capture an image that is shared through other HMDs and/or recorded in memory.

In one embodiment, the virtual display panels are maintained level relative to an artificial horizon and facing directly towards the surgeon, and the surgeon can provide input to the computer equipment 620, e.g., via the HMD 750, to separately adjust azimuth, elevation and size parameters controlling display of each virtual display panel. In another embodiment, the surgeon can provide input to the computer equipment 620, e.g., via the HMD 750, to adjust position of the virtual display panels in 6-degrees of freedom. The radius of the sphere (virtual distance of the virtual display panels from the display screen 752 of the HMD 750) can be adjusted by the surgeon. A default focal radius of about 21 inches between the virtual display panels and the display screen 752 of the HMD 750 may be used.

The size of individual ones of the virtual display panels and/or the size of the collection of virtual display panels may be adjusted by the surgeon. By default, each of the virtual display panels may be sized to approximately fill the field-of-view of the display screen 752 of the HMD 750 (e.g., about 40° diagonal) when the surgeon is looking directly at one of the virtual display panels. In this manner, one virtual display panel can be controlled by the computer equipment 620 to fill the field-of-view of the display screen 752 of the HMD 750 when that display is centered in the field-of-view of the surgeon. By default, the positioning may be defined so that the secondary virtual display panel 722 on the upper row is directly above the operation site (azimuth 0° and elevation about −10°). Another secondary virtual display panel 720 starts just to the left of the secondary virtual display panel 722, and the other secondary virtual display panel 724 starts just to the right of the secondary virtual display panel 722. Distances between the virtual display panels may be defined or adjusted by the surgeon, and the surgeon's preferences may be stored associated with an identifier for the surgeon.

FIG. 12 illustrates that when the surgeon's head tilts further upward above the second pitch threshold so that the surgeon looks along the line-of-sight line 706 above the zone where the virtual display panels 710, 720, 722, and 724 are positioned, or anywhere else in the room except towards the locations of the virtual display panels 710, 720, 722, and 724, the display screen 752 does not display any of the four video streams (e.g., blank display) such that the surgeon may, for example, see that the display screen 752 without observing obstructing video. Thus, in FIG. 12 the virtual display panels 710 720, 722, and 724 are illustrated as below the line-of-sight line 706 of the surgeon, and none would be seen by the surgeon.

As explained above, the operations and methods disclosed herein are not restricted to medical uses. These operations and methods are applicable to many other uses, including industrial uses such as warehousing, manufacturing, product inspection, and/or maintenance.

In one illustrative embodiment, a HMD configured for use in a warehouse environment can provide a plurality of virtual display panels containing different information for guiding a user to a desired location within the warehouse and assisting the user with identifying a product on a shelf. For example, the HMD can respond to a user looking downward by displaying a first virtual display panel which provides directions for traveling to the desired location within the warehouse. An example first virtual display panel may illustrated a virtual pathway (e.g., line) on the ground that the user should follow to reach a desired location where a product resides, etc. in response to the user looking upward, the HMD can responsively display a second virtual display panel that assists the user in identifying the product. An example second virtual display panel may provide descriptive information and/or display a photograph or graphical representation of the product.

Some or all of the operations and methods described herein as being performed by a HMD and/or computer equipment may be performed by a portable computer, such as a laptop computer, tablet computer, mobile phone, data terminal, or wearable computer (e.g., on wrist, arm, leg, etc.). For example, a tablet computer may be configured to select among a plurality of virtual display panels for display on a display device of the table computer and/or on a communicatively connected HMD. The tablet computer may select among the virtual display panels responsive to a user moving (e.g., rotating, pitching, etc.) the tablet computer, responsive to identifying a hand gesture via a camera of the tablet computer and/or via a touch sensitive display of the table computer, and/or responsive to recognizing a voice command via a microphone of the tablet computer. A user may, for example, rotate the tablet computer horizontally to scroll through a plurality of virtual display panels that are virtually organized along a horizontal plane. The user may similarly rotate the table computer vertically to scroll through a plurality of virtual display panels that are virtually organized along a vertical plane. The portable computer (e.g., tablet computer) may be used to control display of the virtual display panels on a communicatively connected HMD. For example, the user may make a hand gesture that is sensed by the portable computer (e.g., via touch sensitive display, proximity sensor, and/or camera), the portable computer can communicate the command to computer equipment which then changes which of a plurality of virtual display panels are displayed on the HMD.

Figure 13:
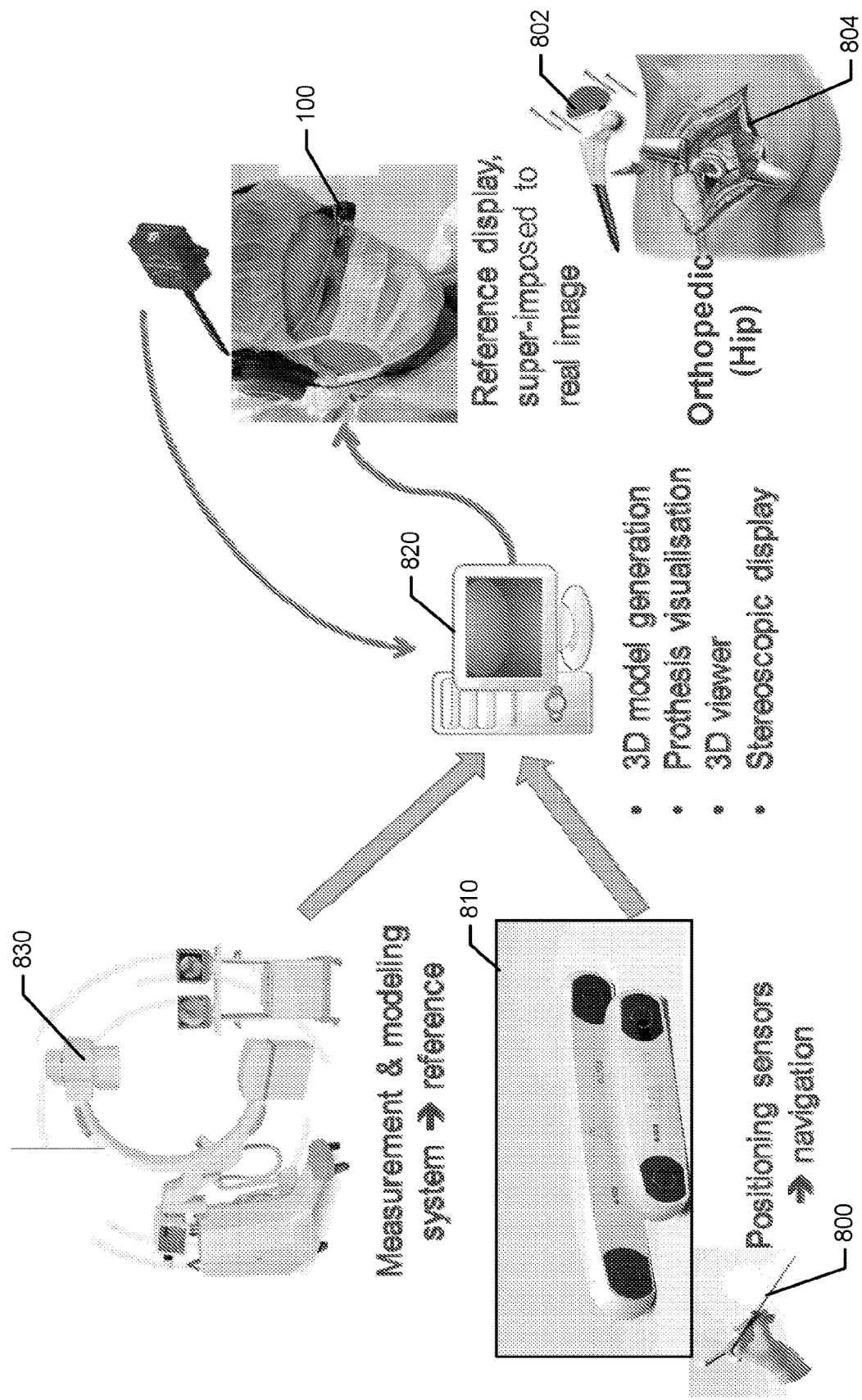
FIG. 13 is a block diagram of components of an augmented reality surgical system that tracks the location of surgical tools, a surgeon's head mounted display, and parts of a patient's anatomy, and generates a three dimensional (3D) model from patient data that is displayed on the head mounted display to be rendered super-imposed at a visually aligned location on the patients body in accordance with some embodiments of the present disclosure.

FIG. 13 is a block diagram of components of an augmented reality surgical system that include a position tracking system 810 (e.g., cameras spaced apart in the operating room) that track the location of a surgical tool 800 and/or prosthetic 802, the HMD 100, and a surgical site 804 or other target location on a patient. A computer system 820 uses patient data from imaging equipment 830 to generate a two dimensional (2D) or three dimensional (3D) model. The imaging equipment 830 may include, without limitation, x-ray equipment, endoscope cameras, magnetic resonance imaging equipment, computed tomography scanning equipment, three-dimensional ultrasound equipment, endoscopic equipment, and/or computer modeling equipment which can generate a multidimensional (e.g., 2D or 3D) model of a targeted site of a patient. The patient data can include real-time feeds and/or earlier stored data from the imaging equipment 830, and may include an anatomical database specific for the particular patient or more generally for humans.

The model can include reference markers or other references that assist with performing correlations between virtual locations in the patient model and physical locations on the patient's body. The computer system 820 uses the present locations of the HMD 100, the surgical site 804, and the surgical tool 800 and/or prosthetic 802 obtained by the position tracking system 810 and uses the reference markers or other references contained in the patient model to transform the patient model to a present perspective view of a wearer of the HMD 100. Some or all of the transformed patient model can then be displayed on the HMD 100 to provide the surgeon with a graphical overlay that is precisely oriented and scaled on the surgical site 804 or other target location on the patient.

The computer system 820 may display graphical representations of the patient model, the tool and/or the prosthetic on the display screen 110 of the HMD 100, and animate movement of the displayed patient mode, tool and/or prosthetic to illustrate a planned procedure relative to a defined location of the surgical site 804 or other target location on the patient's body. The HMD 100 may be communicatively connected to the computer system 820 through a wireless transceiver and/or wired network interface.

The computer system 820 may compare patterns of objects in the video stream from a camera on the HMD 100 to patterns of objects and/or reference markers in the patient model to identify levels of correspondence, and may control transformation of the patient model responsive to identifying a threshold level of correspondence between the compared objects. For example, real-time video captured by the HMD camera during surgery of a patient may be processed by the computer system 820 and compared to video captured by one or more other sources, e.g., the imaging equipment 830. The pattern matching may be constrained to characteristics of an object or a set of objects defined by a surgeon as being relevant to a present procedure.

The computer system 820 can control transformation of the patient model for display on the display screen 110 based on the pattern matching. The computer system 820 may display on the display screen 110 an indicia (e.g., a crosshair or color marker) aligned with an identified object within the video from the HMD camera to assist the surgeon with identifying the corresponding location on the patient. In one embodiment, the computer system 820 displays a graphical indicia on the display screen 110 aligned with one of the anatomical objects displayed on the display screen 110 from the rotated and scaled three dimensional anatomical model responsive to identifying a threshold level of correspondence between a pattern of the one of the anatomical objects and a pattern of one of the anatomical objects in the video stream from the video camera.

The computer system 820 may similarly receive other data and video streams from a patient database and other electronic equipment, which can be selectively displayed on the HMD 100. As used herein, a video stream can include any type of information that can be provided to a display device for display, including without limitation a still image (e.g., digital photo), a sequence of still images, and video having frames provided at a defined frame rate. The computer system 820 can retrieve information relating to a patient's medical history and data obtained by real-time monitoring of a patient, including, for example, hemodynamic, respiratory, and electrophysiological signals.

Although the computer system 820 is illustrated as being separate from the HMD 100, some or all of the operations disclosed herein as being performed by the computer system 820 may additionally or alternatively be performed by one or more processors residing within the HMD 100. Similarly, some of the operations disclosed herein as being performed by the HMD 100 may additionally or alternatively be performed by one or more processors residing within the computer system 820.

Although various embodiments are disclosed in the context of a WAD some other embodiments are directed to tracking the location of a handheld display, such as a tablet computer, and displaying the transformed patient model on the handheld display. The handheld display may include tracking markers, such as on a front surface and/or back surface of the display housing, which are tracked by the position tracking system 810. The handheld display may include a camera that provides a video signal that is combined with a video signal of the transformed patient model from the computer system 820, to display a real world view of the patient augmented with the graphical overlay from a portion of the transformed patient model.

The transformed patient model may additionally be relayed to other HMDs 100 worn by other personnel assisting with the procedure, to other display devices, and/or to a video server for storage. In this manner, other personnel may observe what the surgeon views on the display screen 110.

Figure 14:
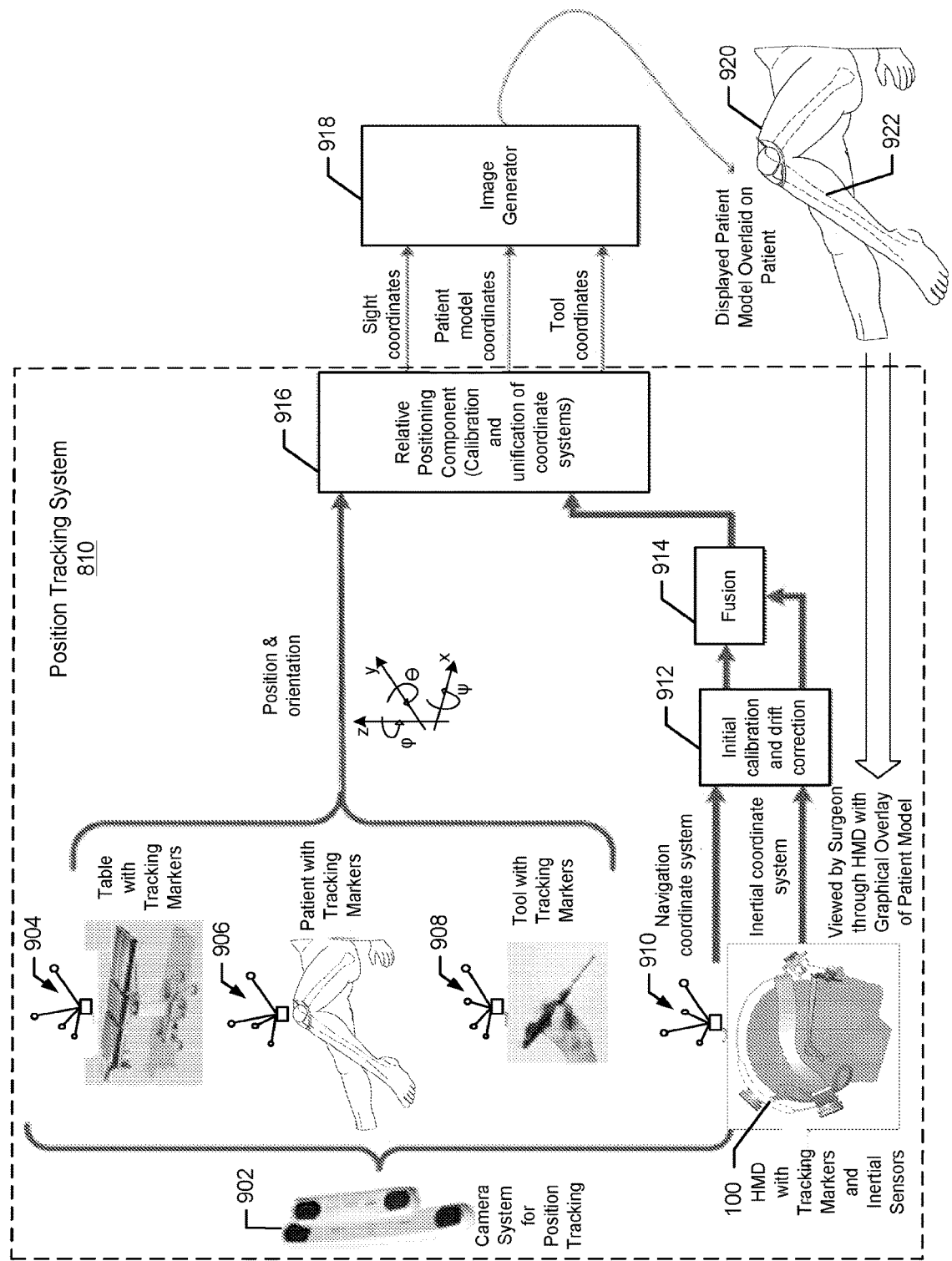
FIG. 14 is another block diagram of the electronic components of the augmented reality surgical system of FIG. 13 according to some embodiments of the present disclosure.

FIG. 14 is another block diagram of the electronic components of the augmented reality surgical system of FIG. 13 according to some embodiments of the present disclosure. Referring to FIG. 14, the position tracking system 810 can include a camera system 902 that tracks the location tracking markers 904 attached to a surgery table, tracking markers 906 attached to patient adjacent to a surgical or other target site, tracking markers 908 attached to a surgery tool and/or prosthetic, and tracking markers 910 attached to the HMD 100. The camera system 902 can include a plurality of cameras that are spaced apart at defined locations within an operating room and each having a field of view that can observe objects to be tracked. In the illustrated example, the camera system. 902 includes two sets of cameras spaced apart by a known distance and relative orientation. The position tracking system 810 may use active optical markers (e.g., light emitting sources), passive optical markers (e.g., light reflectors), but is not limited to the use of cameras. The position tracking system 810 may additionally or alternatively use electromagnetic ranging and trackers, ultrasonic emitters/sensors for ranging and trackers, etc.

Positioning data of the HMD 100 can include navigation coordinate system data determined from the location of the tracking markers 910 attached to the HMD 100, and inertial coordinate system data from the inertial sensors. The navigation coordinate system data and the inertial coordinate system data can be compensated for initial calibration and drift correction over time by a calibration component 912 and combined by a fusion component 914 to output combined HMD position data.

A relative positioning component 916 identifies the relative position and angular orientation of each of the tracked markers 904-910 and the combined HMD position data. The component 916 may perform coordinate transformations of the relative coordinate systems of the surgery table, the patient, the surgery tool, and the HMD 100 to a unified (common) coordinate system. In one embodiment, the relative positioning component 916 outputs sight coordinates data, patient model coordinates data, and tool coordinates data to an image generator 918. The sight coordinates data can be generated based on the combined HMD position data transformed to the unified coordinate system. The patient model coordinates data can be generated based on the position and orientation of the tracking markers 906 attached to the patient transformed to the unified coordinate system, and the tool coordinates data can be generated based on the position and orientation of the tracking markers 908 attached to the surgery tool transformed to the unified coordinate system.

The image generator 918 transforms the patient model (e.g., from the imaging equipment 830) to a present perspective view of a wearer of the HMD 100 mapped to a corresponding object within the FOV of the display screen 110 which is modeled by the patient model. The image generator 918 provides video generated based on the transformed patient model to the HMD 100 for display as a visual model that is dynamically oriented and scaled as a graphical overlay on the surgical site 804 or elsewhere to a corresponding location on the patient where the wearer of the HMD 100 is presently looking and which contains a corresponding object which is modeled by the patient model.

For example, the image generator 918 determines whether any portion of the patient's body is presently within the field of view of what the surgeon sees through the display screen 110 that corresponds to any portion of the transformed patient model. When a portion of the transformed patient model corresponds to a portion of the patient's body within the surgeon's field of view through the display screen 110, the image generator 918 generates video for display on the display screen 110 based on the corresponding portion of the transformed patient model, while translating the portion of the transformed patient model and scaling size of the portion of the transformed patient model to provide an accurately scaled graphical representation of the object that was imaged from the patient or modeled from another source such as an anatomical database.

Thus, for example, when a surgeon's head is rotated so that a portion of a patient's body having a bone that is modeled through CT imagery data becomes within the field of view of the display screen 110, the image generator 918 transforms and scales the patient model of the bone to generate a graphical representation of the bone that is displayed in the display screen 110 as a graphical overlay that matches the orientation and size of the bone from the perspective of the surgeon as-if the surgeon could view the bone through intervening layers of tissue and/or organs.

In the example illustration of block 920, a leg bone model that has been generated, e.g., based on a CT scan of the leg, is transformed and displayed on the display screen 110 to have the accurate six degree of freedom orientation and size relative to the leg bone when viewed as a graphically illustrated representation 922 of the leg bone superimposed on a skin surface of the leg. The surgeon therefore sees the skin surface of the leg through the semitransparent display screen 110 of the HMD 100 with an graphically illustrated representation of the leg bone model overlaid thereon.

Although the graphical representation 922 of the leg bone is illustrated as being displayed in a superimposed position on a skin surface of the leg, the graphical representation 922 can be displayed at other locations which may be controllable by the surgeon. The surgeon may, for example, select to have the graphical representation 922 displayed with a defined offset distance above or below the leg. Moreover, the surgeon may control the size of the displayed graphical representation 922 relative to the leg. The surgeon may, for example, temporarily magnify the displayed graphical representation 922 to view certain details and then return the displayed graphical representation 922 to be scaled and aligned with the leg.

Figure 15:
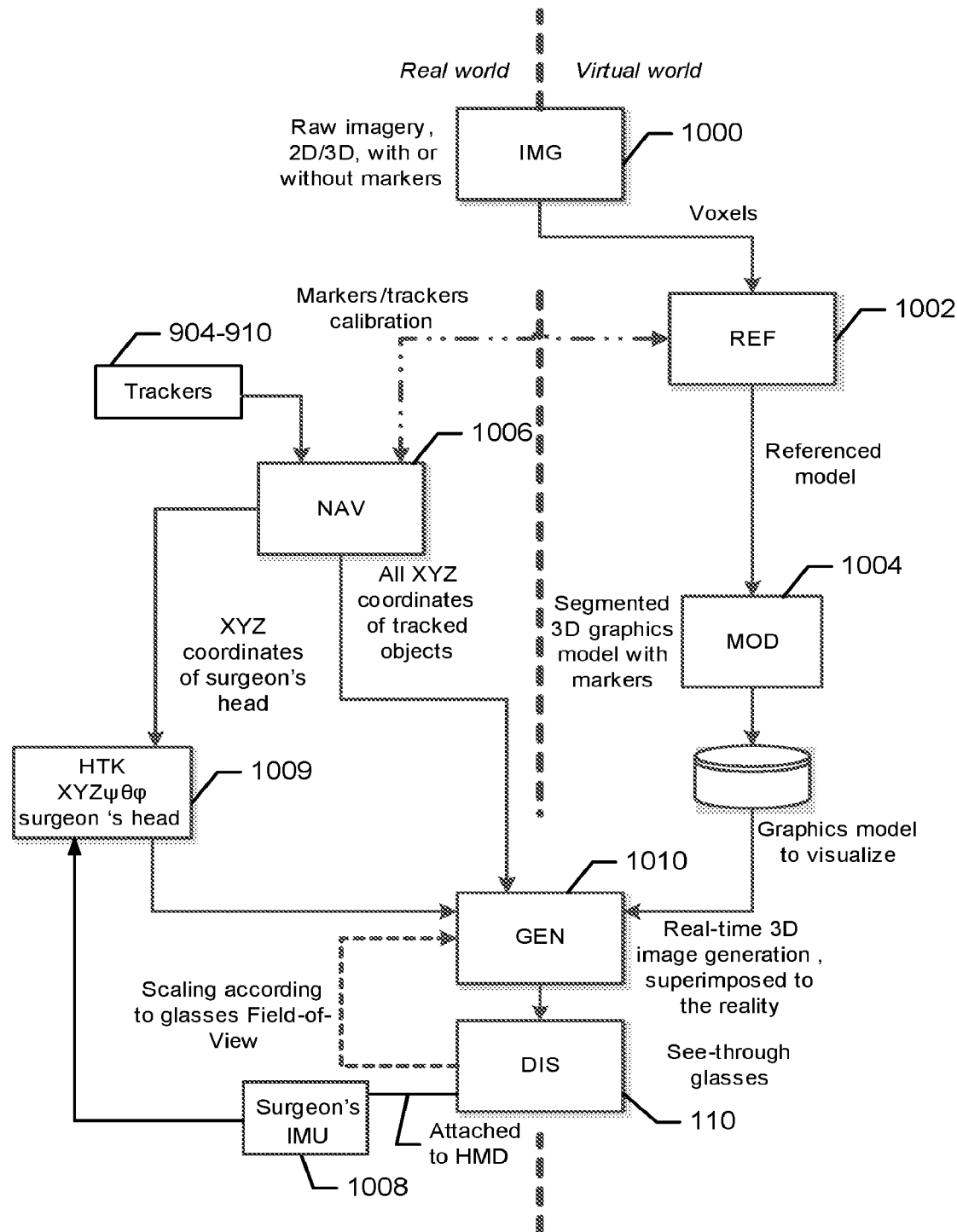
FIG. 15 is another block diagram that illustrates further example operations of electronic system subcomponents of the augmented reality surgical system of FIG. 13 according to some embodiments of the present disclosure.

FIG. 15 is another block diagram that illustrates further example operations of the electronic components of the augmented reality surgical system of FIG. 13 according to some alternative or additional embodiments of the present disclosure. Referring to FIG. 15, the Imagery Device (IMG) 1000 provides x-ray imagery data, e.g. 2D or 3D pictures, with or without reference markers for aiding with location correlation. The image generator 1000 may correspond to the imaging equipment 830 of FIG. 13. The imagery data can be generated before and/or during an operation. For example, real-time generated imagery data from an x-ray device may be used to aid a surgeon with navigating a tool to a target site within a patient during on operation. In another example, 3D imagery data generated days or weeks before an operation can be reused and combined with 2D or 3D x-ray imagery data generated real-time during the operation. The imagery data can be output as a voxelised object, with an accurate 3D geometry of the imaged object.

Calibration of the x-ray device may be performed using an instrumented reference cube. Using an automatic superposition process, all the transformation tables can be determined based on the calibration to provide a clean and rectified geometry of the scanned object, without undesirable deformation. The calibration tables are specific to each x-ray device.

The REF component 1002 accurately references (correlates) the voxelised object in the virtual world to the tracked objects in the real world which may be tracked using the tracking markers explained above or other approaches. The x-ray imagery data can include reference markers which can be created using small objects placed on the imaged object (e.g., patient's body) and which can be readily identified in the x-ray imagery. The reference markers may be invasively attached to the patient (e.g., implanted during an operation by a surgeon) and/or may be non-invasively attached (e.g. adhesively attached to skin).

A modeling component (MOD) 1004 transforms the x-ray imagery data to a 3D patient model (graphical model) which can include reference markers. The patient model may have several separate representations, such as: 1) bones only; 2) skin only; 3) bones and skin; 4) wireframe or color; etc. In case of available articulation between two bones, geometrical transformation between the bones may be defined in the patient model to enable animated movement thereof. The reference markers on articulated bones or other attached objects are referenced in the same coordinate system as the body and/or skeletal model. The number of reference markers may be at least three per rigid object, e.g., bone.

A navigation component (NAV) 1006, which may be a component of the position tracking system 810 of FIG. 14, generates the relative positions (e.g., X, Y, Z coordinate system) of: 1) the targeted body part(s), 2) the HMD 100; 3) surgical tools and/or auxiliary tools; etc. The NAV 1006 identifies the relative positions of the tracked markers, and may further determine the relative angular orientations of the tracked markers 904, 906, 908, and 910. An inertial measurement unit (IMU) 1008 can be mounted to the HMD 100 and configured to sense translational and/or rotational movement and/or static orientation of the surgeon's head, and the sensor data is converted to position data and angular orientation data (e.g., in the inertial coordinate system) by a head tracking (HTK) component 1009. The head tracking component 1009 may perform Kalman filtering on the sensor data to filter noise and/or sensor drift over time when generating the position data and angular orientation data.

A generator component (GEN) 1010 computes in real-time the transformed patient model to be displayed (3D models, symbology, etc.) according to relative positions of the various tracked objects in the operating room. The graphical representation provided by the transformed patient model can be monoscopic or stereoscopic, and can represent several different modes wireframe, color, textured, etc.) that are selectable under surgeon control. The GEN 1010 may perform calibration operations for the NAV 4\1006, the display screen (DIS) 110, the head tracking component 1009, and man-machine interface (e.g., calibration of gesture based control operations, voice based control operations, etc.).

As explained above, the display screen (DIS) 110 can be a see-through display device that is fed video which displays in real-time portions of the transformed patient model and desired symbology, which can be accurately superimposed on the target surgical site or other target area of the patient within the FOV of the surgeon.

Figure 16:
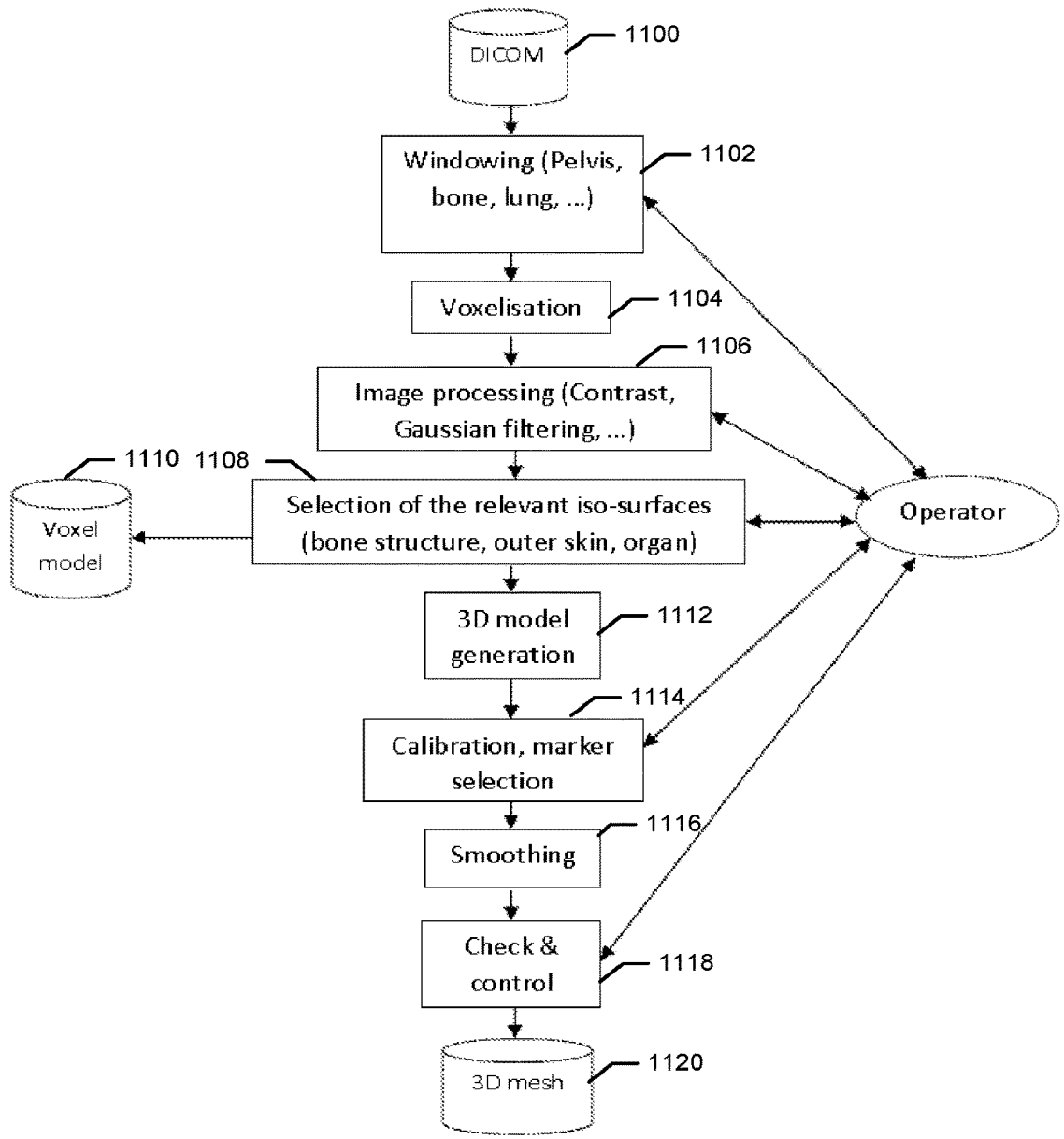
FIGS. 16 and 17 are block diagrams that illustrate further example operations of electronic system subcomponents that can be included in the augmented reality surgical system of FIG. 13 according to some other embodiments of the present disclosure.

FIG. 16 is a block diagram that illustrates further example operations of an electronic system subcomponent that can be included in the augmented reality surgical system of FIG. 13 according to some other embodiments of the present disclosure.

Referring to FIG. 16, the subcomponent accesses CT-SCAN data stored in a DICOM file 1100. The example file 1100 contains raw 3D CT scan data which is cleaned, filtered, and processed through the operations of blocks 1102-1118 to generate a 3D model that is ready for graphical visualization and display on the HMD 100. The geometric structure of the 3D CT scan is based on a set of parallel slices along planes through the patient's body. The slices can have a constant thickness and a shared coordinate system.

Although various embodiments are described in the context of processing 3D CT scan data to generate a graphical model for illustration to an operator, these embodiments are not limited thereto and may be used with any type of patient data that can be graphically modeled for illustration.

The system can adapt its processing of the 3D CT scan data based on knowing what is characterized by the data (e.g., one or more defined organs, one or more defined skeletal structures). The type of information that is extracted from the data can be selected by the operator based on what is desired for graphical visualization through the HMD 100 and/or the type of information may be automatically selected. One selection criterion is based on the X-ray intensity of each pixel per slice. Anatomical structure can be identified and characterized using windowing operations (block 1102) that map X-ray intensity to a contrast intensity image based on parameters that are have predefined for identifying skeletal structure, muscular structure, organ structure, vascular structure, etc. In the embodiment of FIG. 16, the windowing operations processes the types of CT scan data that includes: CT-ABDOMEN, CT-CRANE CT-LUNG, CT-PELVIS, CT-BONE, etc. Output of the windowing operations can be voxelised (block 1104), e.g., by data vectorization based on opacity of the material.

Image processing (block 1106) can then be performed that includes contrast adjustment, Gaussian noise filtering, etc. Selection are made (block 1108) among various available types of modeled iso-surfaces, such as bone, outer skin, organs, etc., based on operator (e.g., surgeon) input and/or other selection criteria. The various types of iso-surface models may be generated using data from the voxel model 1110. A 3D model is generated (block 1112) based on the selections. Calibration information can be generated (block 1114) to facilitate the set-up of the system by performing an initial calibration of the orientation of markers located on the HMD 100, while the operator wears the HMD 100, markers located on the patient, markers located on tools, etc., such as described above regarding FIG. 14. The CT-scan can be performed while markers are fixed to the patient, such as described above. Locations of the markers are correlated to the single coordinate system for all the derived models (voxel or mesh).

Smoothing operations are performed (block 1116) on the resulting data, and data validity checks and operator selective controls are applied (block 1118). A 3D mesh graphical model is generated and can be displayed (block 1120) through the HMD 100 to illustrate the relative position and orientation of a surgical tool, the modeled iso-surfaces from the 3D CT scan data, and any other operator selected and/or defined information. The same coordinate system can be maintained throughout the operations of blocks 1102-1120.

As explained above, the system can generate a graphical model from the patient data that represents detectable anatomical structure that is hidden from direct observation. The system can automatically orient, scale, and display the model so that it is viewable through the HMD 100 superimposed on the relevant area of the physical anatomy of the patient. Thus, for example, when a surgeon's head is rotated so that an area of a patient's body having a bone modeled through CT imagery data becomes within We field of view of the display screen 110 of the HMD 100, the system displays a graphical model of the bone and selected types of anatomical structure (e.g., skeletal structure, muscular structure, organ structure, vascular structure, etc.). The surgeon is thereby able to peer into the patient to view a representation of the bone and/or intervening layers of tissue, organs, etc.

As will be appreciated in view of the present disclosure, previously available procedures that required a surgeon to view static CT scans or other patient data on remote monitors provided limited guidance to the surgeon for where a drill or other surgical tool should be placed on the patient's body and, more particularly, how the drill should be oriented relative to the patient's body so that the drill bit will travel through acceptable structure in the patient's body and reach a target location. Some further embodiments of the present disclosure are directed to displaying additional information through the HMD 100 that provides real-time feedback to the surgeon for where the drill or other tool should be located and oriented before continuing a procedure.

The system can compute and graphically display in real-time through the HMD 100 a projected path that the drill would make through a patient's body based on a present orientation and location of the drill. The surgeon can be allowed to select from among several available visualization modes to have particular anatomical structure and the trajectory of one or more surgical tools graphically modeled and displayed to the surgeon through the HMD 100 based on their computed relative locations, orientations and scaled relationships.

Figure 17:
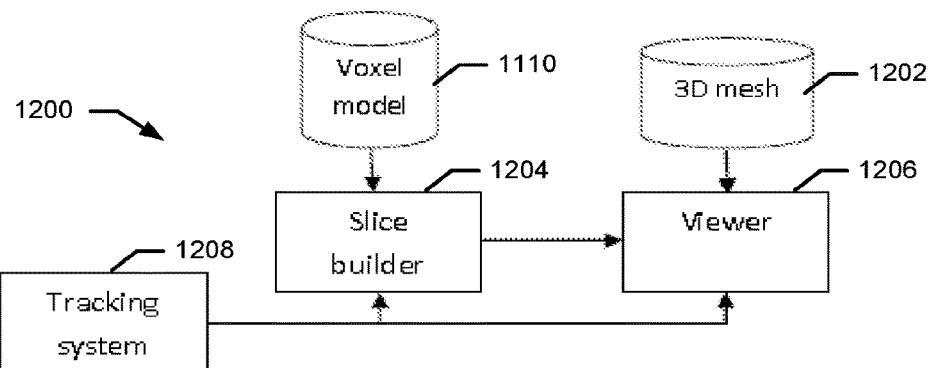
Figure 18:
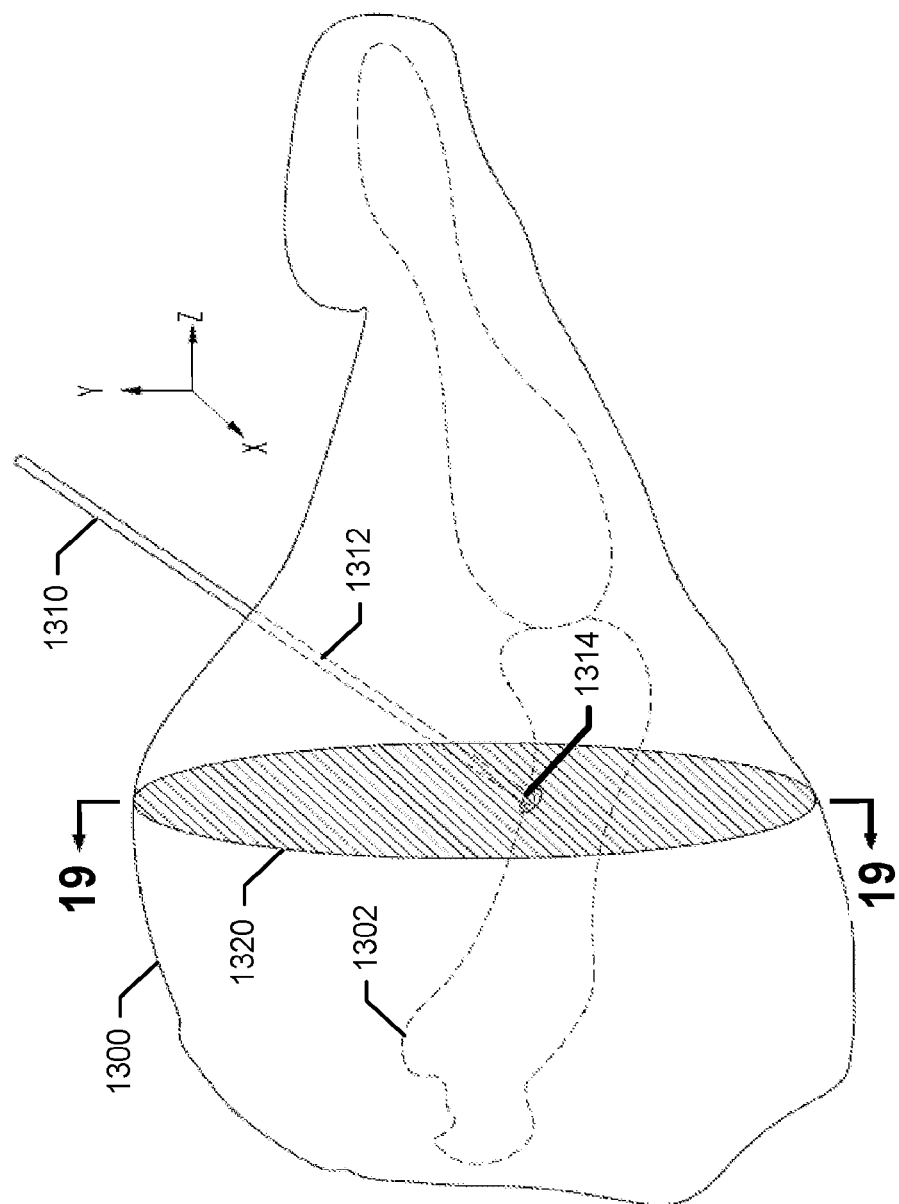
FIG. 18 illustrates a graphical image generated on the head mounted display showing a virtual trajectory of a surgical tool into a patient's anatomy relative to an anatomical model generated from 3D computerized tomography (CT) scan data in accordance with some embodiments of the present disclosure.

FIG. 17 is a block diagram that illustrates further example operations of an electronic system subcomponent 1200 that can be included in the augmented reality surgical system of FIG. 13 to generate the graphical representations of FIGS. 18-23 in according with some embodiments of the present disclosure. FIG. 18 illustrates a graphical image generated on the HMD 100 that shows a virtual trajectory 1312 of a drill bit 1310 extending from a drill or other surgical tool (e.g., scalpel, etc.) into a patient's anatomical bone model 1302 and other selected intervening structure, and which is overlaid at a patient site 1300.

Referring to FIGS. 17 and 18, a tracking system 1208 tracks the relative location and orientation of reference markers attached to the drill bit 1310, the patient site 1300, and the HMD 100, as illustrated in FIG. 14, and computes the relative distance and orientation therebetween. The tracking system 1208 may operate based on the position tracking system 810 described above in FIG. 14, A slice builder component 1204 uses the relative distance and orientation between the drill bit 1310, the patient site 1300, and/or the HMD 100 to select data from the voxel model 1110 that is used to form a slice for display through the HMD 100. Data in the slice may directly correspond to data contained in the voxel model 1110 and/or may be generated from voxel model 1110 data which was obtained from a plurality of 3D CT scans which are intersected by the virtual trajectory 1312 of the drill bit 1310. A viewer component 1206 combines the slice with the 3D mesh model 1202 and displays the combined graphical rendering on the HMD 100 so that it is precisely superimposed on the patient site 1300 from the surgeon's point-of-view. The viewer component 1206 also graphically displays the virtual trajectory 1312, which may be computed using operations based on a ray-tracing type algorithm. In the example of FIG. 18, the viewer component 1206 has also displayed on the HMD 100 a cross sectional slice 1320 that passes through the target location 1314.

The virtual trajectory 1312 can be recomputed and dynamically displayed at a sufficient update rate to provide real-time feedback to a surgeon who is repositioning and reorienting the drill bit 1310 and/or the patient site 1300 so that the virtual trajectory 1312 will intersect a target location 1314. In the example of FIG. 18, the target location 1314 corresponds to a point where the drill bit 1310 would impact the graphically displayed bone model 1302, which is oriented and scaled to match the patient's bone. A sufficient update rate for recomputing and displaying the virtual trajectory 1312 to provide acceptable real-time feedback to a surgeon may be, without limitation, at least 5 Hz.

The system subcomponent 1200 can be configured to provide defined visualization modes that a surgeon can select among using head movement, hand gestures, voice commands, etc., which are sensed by the HMD 100. In some visualization modes the surgeon controls what type of anatomical structure is graphically displayed on HMD 100. For example, the surgeon can select among various visualization modes that control which one or more of the following are displayed on the HMD 100: 1) bone; 2) skin; 3) muscle; 4) organ; 5) vessel; 6) virtual tool trajectory; and 7) cross sectional slice. Another visualization mode can control which cross sectional slices are displayed and/or the orientation of the slice(s) relative to the surgeon's point-of-view. Some visualization modes cause the system subcomponent 1200 to graphically render anatomical structure of the patient for display as wireframes, polygons, or smoothed surfaces, and which can be selectively displayed in monochrome or false colors. A surgeon can dynamically command switching between the available visualization modes and can cause any combination of two more of the visualization modes to be simultaneously active.

Figure 19:
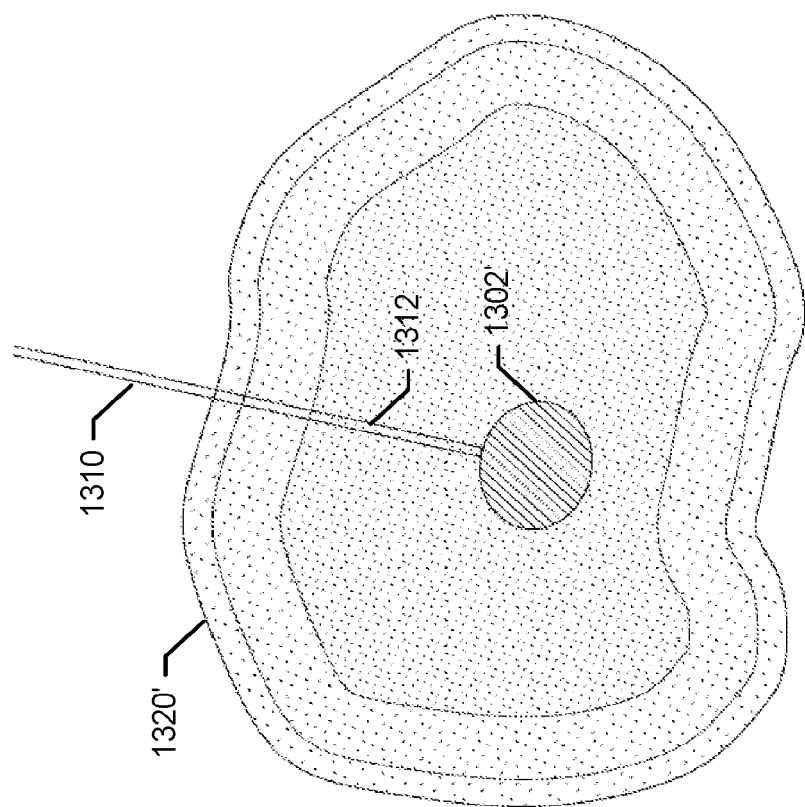
FIG. 19 illustrates another graphical image generated on the head mounted display showing a cross-sectional slice along plane 19-19 in FIG. 18 rotated to provide a front view.

In the example of FIG. 18, the surgeon has selected a visualization mode that displays the slice located at the target location 1314. The slice may be automatically generated and displayed by the viewer 1206 responsive to the target location 1314 being computed based on where the drill bit 1310 will intersect the surface of the graphically displayed bone model 1302 or other selected anatomical structure. FIG. 19 illustrates a portion of the slice 1320 along plane 19-19 in FIG. 18 that has been rotated to provide a front view. The surgeon may select another visualization mode that controls the system subcomponent 1200, e.g., through rotation of the surgeon's head, to rotate the slice 1320 displayed on the HMD 100 from the orientation shown in FIG. 18 to the orientation shown in FIG. 19 along the illustrated x-y coordinate plane, and/or to any other orientation. The slice 1320 can be variably scaled (e.g., zoom-in or zoom-out) for display responsive to commands received from the surgeon. The surgeon can select among various views disclosed here to guide the surgeon's manipulation of the drill hit 1310 or other surgical tool.

Figure 20:
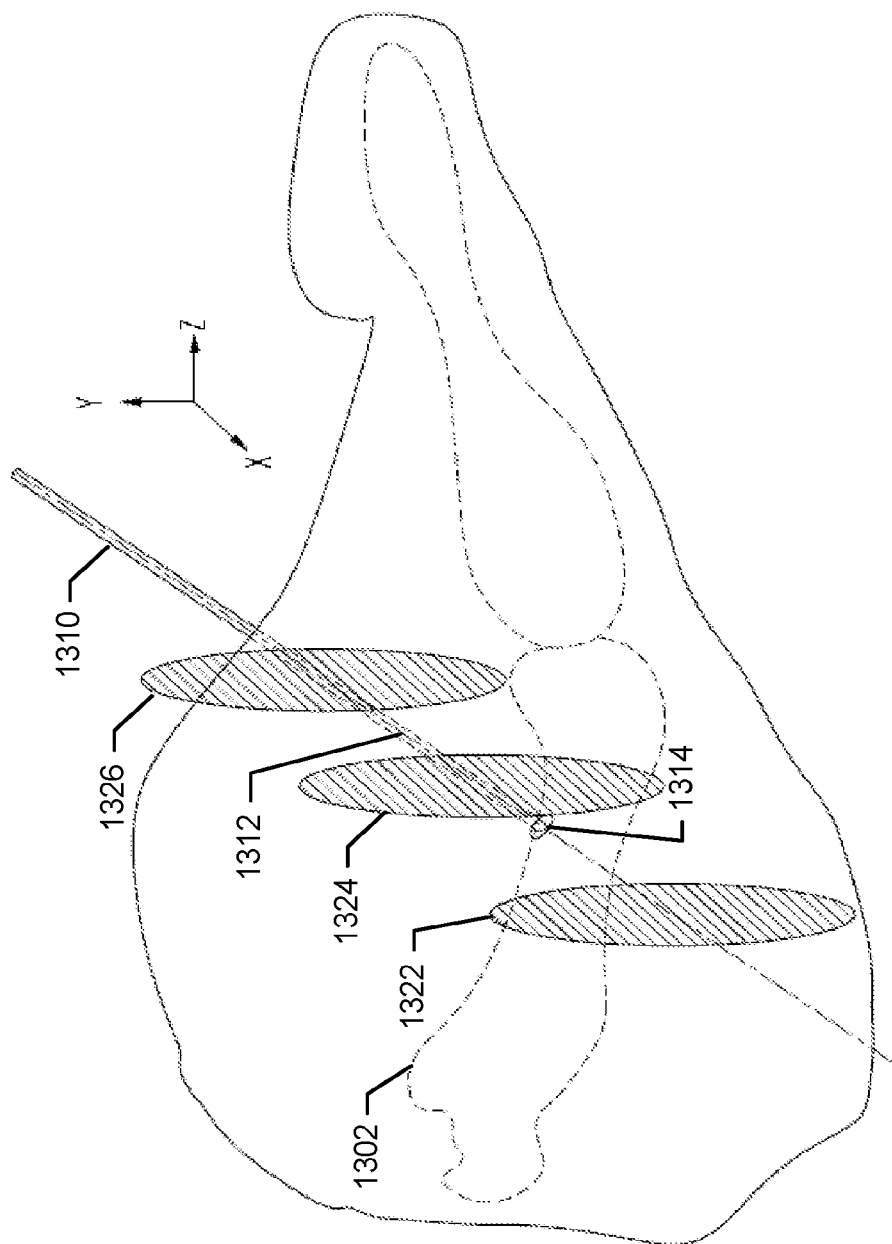
FIG. 20 illustrates another graphical display generated on the head mounted display showing a sequence of cross-sectional slices of the 3D CT scan anatomical model spaced apart along the virtual trajectory of the tool and illustrates points of intersection between the virtual trajectory and the slices.

The surgeon can select another visualization mode that causes the system subcomponent 1200 to simultaneously or sequentially display a sequence of cross-sectional slices that are spaced apart along the virtual trajectory 1312 of the drill bit 1310. An example graphical display generated on the HMD 100 according to this visualization mode is shown in FIG. 20. In the non-limiting example of FIG. 20, three slices 1322, 1324, 1326 are parallel to one another, e.g., parallel to the illustrated x-y coordinate plane, and are spaced apart and each centered along the virtual trajectory 1312. The graphical display shows the spatial relationship between the virtual trajectory 1312 and anatomical structure illustrates in the slices 1322, 1324, 1326, and moreover shows intersection points between the virtual trajectory 1312 and each of the slices 1322, 1324, 1326. The surgeon can control the system subcomponent 1200 to rotate and/or scale all three slices 1322, 1324, 1326 or a selected one or more thereof. The slices are selected based on the computer determining that the slice contains imaging data of a location within the patient that is intersected by the virtual trajectory 1312. The surgeon can control how many slices are simultaneously displayed and can control where a slice is generated and displayed along the virtual trajectory 1312. For example, through a head movement, hand gesture, or other command the surgeon may move a pointer along the virtual trajectory 1312 to select a location where a slice, e.g., along the x-y plane, is to be generated and displayed on the HMD 100.

Figure 21:
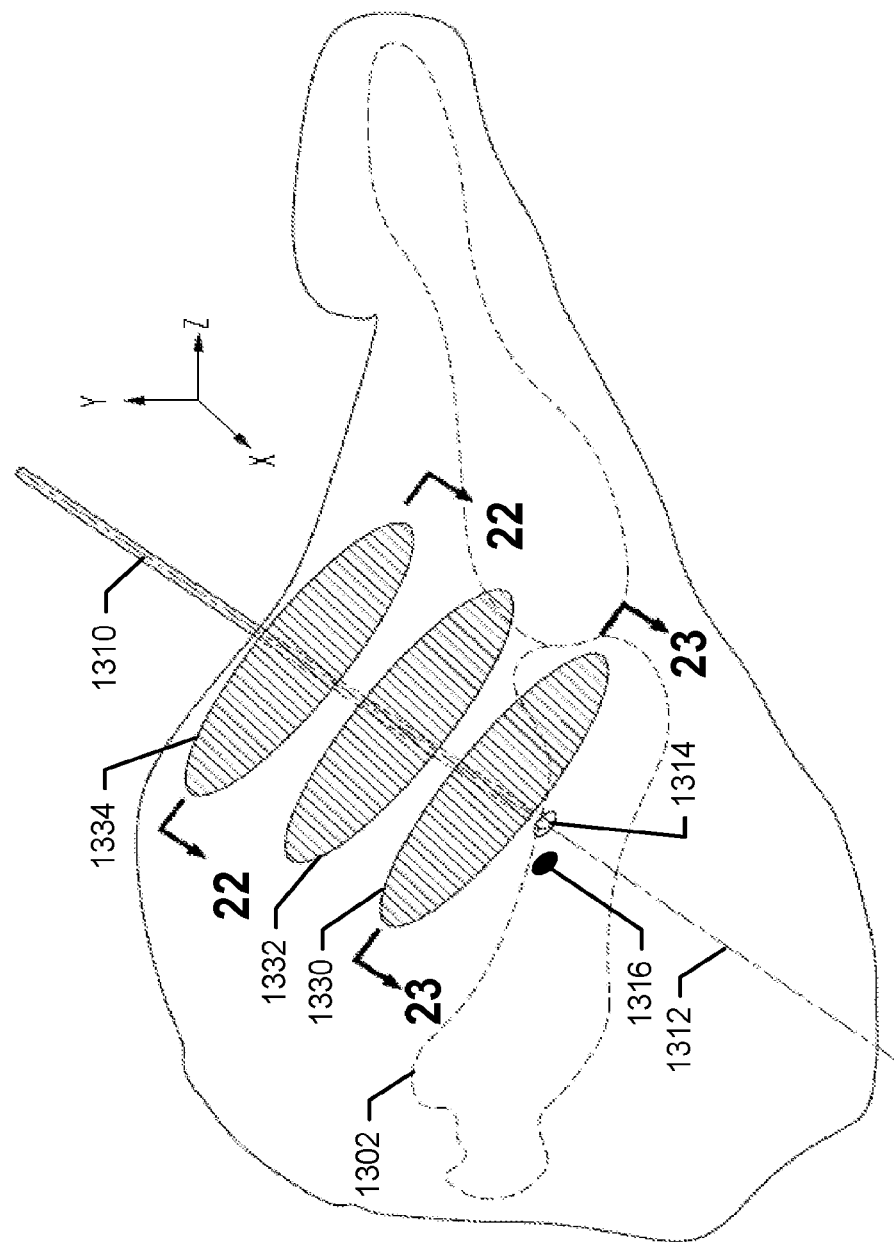
FIG. 21 illustrates another graphical display generated on the head mounted display showing a sequence of cross-sectional slices of the 3D CT scan anatomical model spaced apart along the virtual trajectory of the tool and oriented in planes perpendicular to the virtual trajectory of the tool.

The surgeon can select another visualization mode that causes the system subcomponent 1200 to simultaneously or sequentially display another sequence of cross-sectional slices that are spaced apart along the virtual trajectory 1312 of the drill bit 1310 and oriented in parallel planes that are perpendicular to the virtual trajectory 1312. An example graphical display generated on the HMD 100 according to this visualization mode is shown in FIG. 21. In the non-limiting example of FIG. 21, three slices 1330, 1332, 1334 are parallel to one another and spaced apart and each centered along the virtual trajectory 1312. The surgeon can control the system subcomponent 1200 to rotate and/or scale all three slices 1330, 1332, 1334 or a selected one or more thereof. The surgeon can control how many slices are simultaneously displayed and can control where a slice is generated and displayed along the virtual trajectory 1312, and may control how many dimensions are illustrated in the various view and/or can select among various perspective views. The surgeon may furthermore control whether the graphical display renders a three dimensional or orthographic projection view of the graphical anatomical model and/or slices thereof.

The visualization mode that is displayed in FIG. 21 provides the surgeon with a view from the perspective of looking-down the drill bit 1310. A graphical display illustrates to the surgeon the virtual trajectory 1312 and a tool impact location 1314 where the drill bit 1310 is projected to make contact with the bone if the surgeon proceeded to drill while maintaining the present orientation of the drill hit 1310. The graphical display may also illustrate a target location 1316 that the surgeon has earlier defined as being a desired location where the drill bit 1310 should contact the bone. Simultaneous illustration of the tool impact location 1314 and the target location 1316 in this manner can be a particularly useful view mode while a surgeon is seeking to position and orient the drill bit 1310 to intersect or to avoid intersecting various anatomical structure illustrated by one or more of the slices 1330, 1332, 1334 and/or other slices selected by the surgeon, and while accomplishing the objective of guiding the drill bit 1310 to contact the target location 1316 on the bone. Through a head movement, hand gesture, or other command the surgeon may move a pointer along the virtual trajectory 1312 to select a location where a perpendicular slice is to be generated and displayed on the HMD 100.

Figure 23:
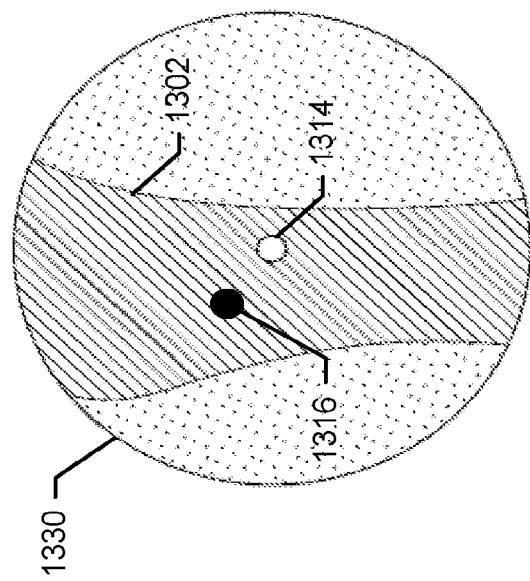
FIGS. 22 and 23 each illustrate a graphical image generated on the head mounted display showing the cross-sectional slices along planes 22-22 and 23-23, respectively, in FIG. 21 rotated to provide a front view.
Figure 22:
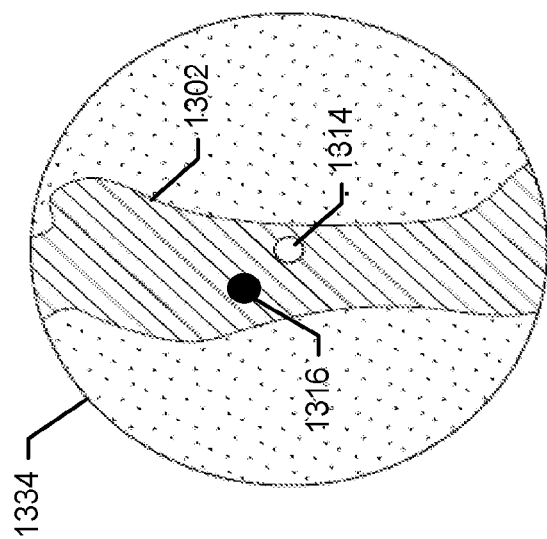

In a further visualization mode, the surgeon can control the system subcomponent 1200 to rotate and/or scale one or more of the slices 1330, 1332, 1334. FIG. 22 illustrates the slice 1334 along plane 22-22 in FIG. 21 rotated to provide a front view, and illustrates the tool impact location 1314 where the drill bit 1310 would impact the graphically displayed bone model 1302 based on a present location and orientation of the drill bit 1310 relative to the patient site 1300 and further illustrates the target location 1316. FIG. 23 illustrates the slice 1330 along plane 23-23 in FIG. 21 rotated to provide a front view, and illustrates the tool impact location 1314 where the drill bit 1310 would impact the graphically displayed bone model 1302 based on a present location and orientation of the drill bit 1310 relative to the patient site 1300 and further illustrates the target location 1316. The surgeon may control the system subcomponent 1200, e.g., through rotation of the surgeon's head, to rotate and/or scale one or more of the slices displayed on the HMD 100. The surgeon may furthermore control the system subcomponent 1200 to selectively display any one or more of the virtual trajectory 1312, the tool impact location 1314, and the target location 1314.

In this manner various embodiments of the present disclosure displaying information through the HMD 100 that provides real-time guidance and feedback to a surgeon who seeks to position and orient a surgical tool to reach a target location within a patient.

Further Definitions And Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic magnetic optical, electromagnetic, or semiconductor system, apparatus, or device or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method for performing a surgical procedure, said method comprising:
   providing an augmented reality surgical system including:
      a display comprising a see-through display screen that display images while allowing transmission of ambient light therethrough;
      a motion sensor connected to the display and configured to output a motion signal indicating measured movement of the display; and
      at least one camera configured to observe a first set of reference markers connected to a patient, and a second set of reference markers connected to a surgical tool located within a surgical room; and
      a computer,
   computing the relative location and orientation of the display and the first and second set of reference markers;
   generating a three dimensional anatomical image using patient data created by medical imaging equipment that has imaged a portion of the patient;
   generating a video signal based on at least a portion of the three dimensional anatomical image and the location and orientation of the first and second set of reference markers coupled to the patient and the surgical instrument; and
   output a video signal to the display screen on the display,
   wherein the computer is configured to animate movement of a displayed graphical representation of the patient, surgical tool or surgical site to illustrate a planned procedure relative to a defined location of the surgical site or other targeted anatomical site.

2. The method of claim 1, further comprising displaying a graphical representation on the display screen of the at least a portion of a three dimensional anatomical model oriented and scaled to provide a displayed overlay on the portion of the patient that was imaged by the medical imaging equipment.

3. The method of claim 1, further comprising displaying a graphical representation of a medical procedure on the display overlaid on the portion of the patient that was imaged by the medical imaging equipment.

4. A method for performing a surgical procedure, said method comprising:
   providing an augmented reality surgical system including:
      a positioning tracking system; and
      a computer system
   tracking a location of a surgical tool, a head mounted display, and a surgical site via the positioning tracking system;
   generating an image model of a targeted site of the patient by the computer system using patient data from an imaging device, wherein the image model includes reference markers that assist in correlating between virtual locations and physical locations of the patient;
   processing, by the computer system, the present locations the head mounted display, the surgical site and the surgical tool obtained by the positioning tracking system; and
   generating a graphical representation of the patient to the head mounted display for a user to view, wherein the graphical representation is generated using the reference markers contained in the image model to generate,
   wherein the computer system is configured to animate movement of the displayed graphical representation of the patient, surgical tool or surgical site to illustrate a planned procedure relative to a defined location of the surgical site or other targeted anatomical site.

5. The method of claim 4, further comprising displaying graphical representations of the surgical tool or surgical site on the display screen of the head mounted display.

6. The method of claim 4, wherein imaging device may include one of an x-ray device, endoscope cameras, magnetic resonance imaging equipment, computed tomography scanning equipment, three-dimensional ultrasound equipment, and endoscopic equipment.

7. The method of claim 4, wherein the computer may receive non-image patient data and display the non-image data into a graphical representation to be displayed on the head mounted display.

8. The method of claim 4, wherein the positioning tracking system includes a plurality of cameras spaced apart at defined locations within an operating room and each having a field of view that can observe objects to be tracked.

9. The method of claim 4, wherein the positioning tracking system may use electromagnetic ranging and trackers, ultrasound emitters/sensors for ranging and trackers.

10. A method for displaying multiple video streams to a user during a surgical procedure, said method comprising:
    providing an augmented reality surgical system including:
       a display comprising a see-through display screen that display images while allowing transmission of ambient light therethrough;
       a motion sensor connected to the display and configured to output a motion signal indicating measured movement of the display; and
       a computer configured to receive a plurality patient data including a three dimensional anatomical image of the patient and relative location and orientation of the patient and to control which or all of the plurality of patient data to output as a video signal to the display screen,
       outputting the video signal to the display screen,
    wherein the computer is configured to animate movement of a displayed graphical representation of the patient, surgical tool or surgical site to illustrate a planned procedure relative to a defined location of the surgical site or other targeted anatomical site.

11. The method of claim 10, wherein: the computer is communicatively connected to a data server to receive the patient data, one of the which is a data generated by medical imaging equipment, another one of the patient data is information from a patient database defining a patient's medical history, and another one of the patient data comprises data generated by medical equipment based on real-time monitoring of the patient's vitals.

12. The method of claim 10, wherein: the computer is configured to convert the patient data into a graphical display and to output the selected one or all of the plurality of patient data into video streams as a video signal to the display screen.

13. The method of claim 10, wherein the computer communicates video from the video camera through a network to another display worn by another person.

14. The method of claim 10, wherein the computer provides a graphical representation of a virtual trajectory of a surgical tool to the patient's surgical site.

15. The method of claim 10, wherein the surgical tool is a drill bit.

* * * * *